(12) United States Patent
Cho et al.

(10) Patent No.: US 10,189,916 B2
(45) Date of Patent: Jan. 29, 2019

(54) TRANSITION METAL COMPOUND AND CATALYST COMPOSITION INCLUDING THE SAME

(71) Applicant: LG CHEM, LTD., Seoul (KR)

(72) Inventors: Yoon Hee Cho, Daejeon (KR); Jung Ho Jun, Daejeon (KR); Jin Sam Gong, Daejeon (KR); Choong Hoon Lee, Daejeon (KR); Seung Hwan Jung, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/538,324

(22) PCT Filed: Jul. 1, 2016

(86) PCT No.: PCT/KR2016/007145
§ 371 (c)(1),
(2) Date: Jun. 21, 2017

(87) PCT Pub. No.: WO2017/003262
PCT Pub. Date: Jan. 5, 2017

(65) Prior Publication Data
US 2017/0349674 A1    Dec. 7, 2017

(30) Foreign Application Priority Data
Jul. 2, 2015   (KR) .................. 10-2015-0094692

(51) Int. Cl.
| | | |
|---|---|---|
| C07F 17/00 | (2006.01) | |
| C08F 4/6592 | (2006.01) | |
| C07D 215/02 | (2006.01) | |
| C07D 333/76 | (2006.01) | |
| C07F 7/00 | (2006.01) | |
| C07F 7/28 | (2006.01) | |
| C08F 10/00 | (2006.01) | |
| C08F 4/64 | (2006.01) | |
| C08F 10/02 | (2006.01) | |
| C08F 210/16 | (2006.01) | |

(52) U.S. Cl.
CPC .......... *C08F 4/6592* (2013.01); *C07D 215/02* (2013.01); *C07D 333/76* (2013.01); *C07F 7/00* (2013.01); *C07F 7/28* (2013.01); *C07F 17/00* (2013.01); *C08F 4/64* (2013.01); *C08F 10/00* (2013.01); *C08F 10/02* (2013.01); *C08F 210/16* (2013.01)

(58) Field of Classification Search
CPC .............................. C07F 17/00; C08F 4/6592
See application file for complete search history.

(56) References Cited

U.S. PATENT DOCUMENTS

| | | |
|---|---|---|
| 5,064,802 A | 11/1991 | Stevens et al. |
| 6,548,686 B2 | 4/2003 | Nabika et al. |
| 7,381,679 B2 * | 6/2008 | Rieger .................... C08F 10/06 502/103 |
| 2004/0220050 A1 | 11/2004 | Frazier et al. |
| 2004/0242880 A1 | 12/2004 | Mihan et al. |
| 2007/0015657 A1 | 1/2007 | Rieger et al. |
| 2010/0062927 A1 | 3/2010 | Lee et al. |
| 2011/0172451 A1 | 7/2011 | Lee et al. |
| 2011/0177935 A1 | 7/2011 | Lee et al. |
| 2013/0203949 A1 | 8/2013 | Lee et al. |
| 2013/0211020 A1 | 8/2013 | Lee et al. |
| 2013/0211021 A1 | 8/2013 | Lee et al. |
| 2013/0211023 A1 | 8/2013 | Lee |
| 2013/0211024 A1 | 8/2013 | Lee et al. |
| 2015/0011770 A1 | 1/2015 | Lee et al. |
| 2015/0094435 A1 | 4/2015 | Cho et al. |
| 2015/0361196 A1 | 12/2015 | Do et al. |

FOREIGN PATENT DOCUMENTS

| | | |
|---|---|---|
| CN | 1753914 A | 3/2006 |
| KR | 10-0976131 B1 | 8/2010 |
| KR | 10-0986301 B1 | 10/2010 |
| KR | 10-1501853 B1 | 3/2015 |
| KR | 10-2015-0034652 A | 4/2015 |
| WO | WO 03/024982 A1 | 3/2003 |
| WO | WO 2015/046930 A1 | 4/2015 |

OTHER PUBLICATIONS

Deisenhofer et al., "Asymmetric Metallocene Catalysts Based on Dibenzothiophene: A New Approach to High Molecular Weight Polypropylene Plastomers," Organometallics, vol. 22, No. 17, Aug. 18, 2003 (published on web Jul. 22, 2003), pp. 3495-3501.

Partial Supplementary European Search Report for European Application No. 16818295.4, dated Jul. 25, 2017.

Chen et al., "A Novel Phenolate "Constrained Geometry" Catalyst System. Efficient Synthesis, Structural Characterization, and αOlefin Polymerization Catalysis", Organometallics, 1997, vol. 16, No. 26, pp. 5958-5963.

Christie et al., Novel Routes to Bidentate Cyclopentadineyl-Alkoxide Complexes of Titanium: Synthesis of $(\eta^5\text{-}\rho\text{-}C_5R^1{}_4CHR^2CH_2CR^3R^4O)TiCl_3$, Organometallics, 1999, vol. 18, pp. 348-359.

Gibson et al., "Advances in Non-Metallocene Olefin Polymerization Catalysis", Chem. Rev., 2003, vol. 103, pp. 283-315.

Gielens et al., "Titanium Hydrocarbyl Complexes with a Linked Cyclopentadienyl-Alkoxide Ancillary Ligand; Participation of the Ligand in an Unusual Activation of a (Trimethylsilyl)methyl Group", Organometallics, 1998, vol. 17, pp. 1652-1654.

(Continued)

*Primary Examiner* — Caixia Lu

(74) *Attorney, Agent, or Firm* — Birch, Stewart, Kolasch & Birch, LLP

(57) ABSTRACT

The present disclosure provides a novel transition metal compound having excellent structural stability together with polymerization reactivity, and thereby is useful as a catalyst in preparing an olefin-based polymer, particularly, a low density olefin-based polymer, and a catalyst composition including the same.

7 Claims, No Drawings

(56) References Cited

OTHER PUBLICATIONS

International Search Report, issued in PCT/KR2016/007145, dated Oct. 11, 2016.
Kim et al., "Preparation of Thiophene-Fused and Tetrahydroquinoline-Linked Cyclopentadienyl Titanium Complexes for Ethylene/α-Olefin Copolymerization", Catalysts, 2013, vol. 3, pp. 104-124.
Rau et al., "Synthesis and application in high-pressure polymerization of a titanium complex with a linked cyclopentadienyl-phenoxide ligand", Journal of Organometallic Chemistry, Aug. 25, 2000, vol. 608, Issues 1-2, pp. 71-75.
Technical Information of ENGAGE 8842. Nov. 30, 2000, <URL:http://dowglobal.ides.com/docselect.aspx?l=48244&E=49414&DOC=DOWTDS&DS=123&DK=STD&DC=en>.
Turner et al., "Facile resolution of constrained geometry indenyl-phenoxide ligation", Chem. Commun., 2003, pp. 1034-1035.
Zhang et al., "Constrained Geometry Tetramethylcyclopentedienyl-phenoxytitanium Dichlorides: Template Synthesis, Structures, and Catalytic Properties for Ethylene Polymerization", Organometalilcs, 2004, vol. 23, No. 3, pp. 540-546.
European Search Report for Appl. No. 16818295.4 dated Nov. 8, 2017.
XP 002774615, The Dow Chemical Company, Technical Information of Engage 8180, Nov. 30, 2000, Retrieved from the Internet: URL:http://dowglobal.ides.comjdocselect.aspx?l=48244&E=30953&DOC=DOWTDS&DS=123&DK=STD&DC=en.
XP 055415013, The Dow Chemical Company, Technical Information of Engage 7447, May 1, 2008, Retrieved from the Internet: URL:http://msdssearch.dow.com/PublishedliteratureDOWCOM/dh0134/0901b80380134edb.pdf?filepath=elastomers/pdfs/noreg/774-00027.pdf&fromPage=GetDoc.
XP 055415019, The Dow Chemical Company, Technical Information of Engage 7467, May 1, 2008, Retrieved from the Internet, URL:http://msdssearch.dow.com/PublishedliteratureDOWCOM/dh0134/0901b80380134ee7.pdf?filepath=elastomers/pdfs/noreg/774-00028.pdf&fromPage=GetDoc.
Chinese Office Action and Search Report, dated Nov. 12, 2018 for Chinese Application No. 201680005117.6, with an English translation of the Chinese Office Action.
Lin, "Introduction to Petrochemical Catalysis," Petroleum Industry Press, Jun. 2008, pp. 255-270 (48 pages total), with an English translation.

* cited by examiner

TRANSITION METAL COMPOUND AND CATALYST COMPOSITION INCLUDING THE SAME

FIELD OF THE INVENTION

This application claims priority to and the benefits of Korean Patent Application No. 10-2015-0094692 filed with the Korean Intellectual Property Office on Jul. 2, 2015, the entire contents of which are incorporated herein by reference.

The present disclosure relates to a novel transition metal compound and a catalyst composition including the same.

DESCRIPTION OF THE RELATED ART

Dow Chemical Company introduced [Me$_2$Si(Me$_4$C$_5$)NtBu]TiCl$_2$ (Constrained-Geometry Catalyst, abbreviated as CGC hereinafter) in early 1990s (U.S. Pat. No. 5,064,802), and advantages of the CGC in a copolymerization reaction of ethylene and alpha-olefin compared to metallocene catalysts that have been known in the art may be summarized into two points as follows: (1) CGC produces a high molecular weight polymer while exhibiting high activity even at high polymerization temperatures, and (2) copolymerizability of alpha-olefin having large steric hindrance such as 1-hexene and 1-octene is very improved as well. Besides, as other properties of CGC in a polymerization reaction have been gradually known, efforts to synthesize derivatives of CGC to use as a polymerization catalyst have been actively made both in academics and industries.

As one of the approaches, syntheses of metal compounds, in which other various bridges instead of a silicon bridge and nitrogen substituents are introduced, and polymerization thereof have been tried. Representative metal compounds that have been known until recently may be listed as the following Compounds (1) to (4) (Chem. Rev. 2003, 103, 283).

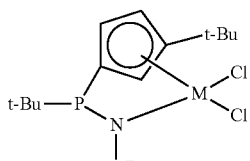

(1)

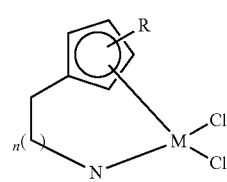

(2)

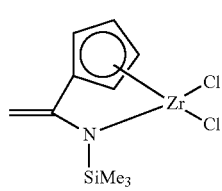

(3)

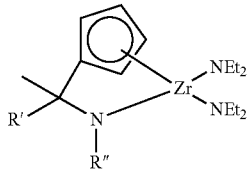

(4)

In Compounds (1) to (4), phosphorous (1), ethylene or propylene (2), methylidene (3) and methylene (4) bridges are introduced, respectively, instead of a silicon bridge of a CGC structure, however, improved results in terms of activity or copolymerization performance were not able to be obtained compared to CGC when Compounds (1) to (4) were used in ethylene polymerization or copolymerization with alpha-olefin.

In addition, as another approach, compounds having an oxido ligand instead of an amino ligand of the CGC have been actively synthesized, and polymerization using the same has also been tried in some cases. Examples thereof are summarized as follows.

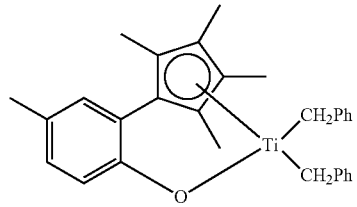

(5)

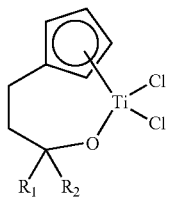

(6)

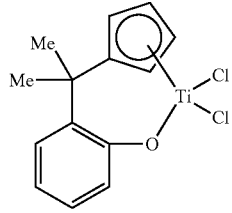

(7)

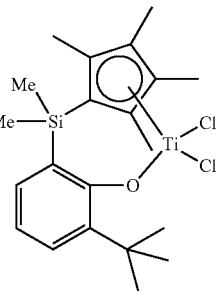

(8)

Compound (5) has been reported by T. J. Marks et al. and has a cyclopentadiene (Cp) derivative and an oxido ligand being cross-linked by an ortho-phenylene group (Organometallics 1997, 16, 5958). Compounds having the same cross-linkage and polymerization using the same have also been reported by Mu et al. (Organometallics 2004, 23, 540). In addition, an indenyl ligand and an oxido ligand being cross-linked by the same ortho-phenylene group has been reported by Rothwell et al. (Chem. Commun. 2003, 1034). Compound (6) has been reported by Whitby et al., and has a cyclopentanienyl ligand and an oxido ligand being bridged by 3 carbons (Organometallics 1999, 18, 348), and such catalysts have been reported to exhibit activity for syndiotactic polystyrene polymerization. Similar compounds have also been reported by Hessen et al. (Organometallics 1998, 17, 1652). Compound (7) has been reported by Rau et al., and exhibits activity for ethylene polymerization and ethylene/1-hexene copolymerization at a high temperature and a high pressure (210° C., 150 mPa) (J. Organomet. Chem. 2000, 608, 71). After that, Sumitomo Corporation applied for a patent on the synthesis of catalysts having similar structures thereto (8) and high temperature and high pressure polymerization using the same (U.S. Pat. No. 6,548,686). However, among the above-mentioned attempts, only a small number of catalysts are actually used in commercial factories. Accordingly, catalysts exhibiting enhanced polymerization efficiency, and simple methods for preparing such catalysts have been required.

DISCLOSURE OF THE INVENTION

Technical Problem

The present disclosure is directed to providing a novel transition metal compound having excellent polymerization reactivity and structural stability, and thereby useful in preparing an olefin-based polymer, particularly, a low density olefin-based polymer.

The present disclosure is also directed to providing a catalyst composition including the transition metal compound, and thereby useful in preparing an olefin-based polymer, particularly, a low density olefin-based polymer.

The present disclosure is also directed to providing an olefin-based polymer prepared using the catalyst composition including the transition metal compound.

The present disclosure is also directed to providing a ligand compound useful in preparing the transition metal compound.

Technical Solution

The present disclosure has been made in view of the above, and one embodiment of the present disclosure provides a transition metal compound of the following Chemical Formula 1:

[Chemical Formula 1]

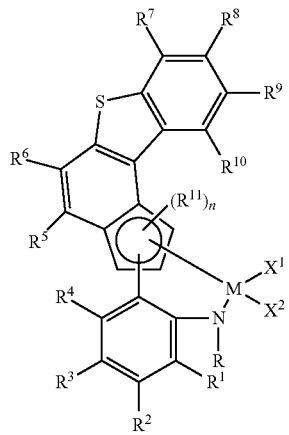

In Chemical Formula 1,

M is a group 4 transition metal,

R is selected from the group consisting of a hydrogen atom, an alkyl group having 1 to 20 carbon atoms, a cycloalkyl group having 3 to 20 carbon atoms, an aryl group having 6 to 20 carbon atoms, an arylalkyl group having 7 to 20 carbon atoms, an alkylaryl group having 7 to 20 carbon atoms and combinations thereof; or R and $R^1$ are linked to each other to form an aliphatic ring having 3 to 20 carbon atoms or an aromatic ring having 5 to 20 carbon atoms including N, $R^1$ to $R^{10}$ are each independently selected from the group consisting of a hydrogen atom, a halogen group, an alkyl group having 1 to 20 carbon atoms, an alkenyl group having 2 to 20 carbon atoms, a cycloalkyl group having 3 to 20 carbon atoms, an aryl group having 6 to 20 carbon atoms, an arylalkyl group having 7 to 20 carbon atoms, an alkylaryl group having 7 to 20 carbon atoms, an alkoxy group having 1 to 20 carbon atoms, an aryloxy group having 6 to 20 carbon atoms, a silyl group and combinations thereof, or adjacent two or more functional groups among $R^1$ to $R^{10}$ are linked to each other to form an aliphatic ring having 3 to 20 carbon atoms or an aromatic ring having 6 to 20 carbon atoms, $R^{11}$ is selected from the group consisting of an alkyl group having 1 to 20 carbon atoms, an alkenyl group having 2 to 20 carbon atoms, a cycloalkyl group having 3 to 20 carbon atoms, an aryl group having 6 to 20 carbon atoms, an arylalkyl group having 7 to 20 carbon atoms, an alkylaryl group having 7 to 20 carbon atoms, a silyl group, and a metalloid radical of a group 14 metal substituted with a hydrocarbyl group having 1 to 20 carbon atoms, $X^1$ and $X^2$ are each independently selected from the group consisting of a halogen group, an alkyl group having 1 to 20 carbon atoms, an alkenyl group having 2 to 20 carbon atoms, an aryl group having 6 to 20 carbon atoms, an alkylaryl group having 7 to 20 carbon atoms, an arylalkyl group having 7 to 20 carbon atoms, an alkylamino group having 1 to 20 carbon atoms, an arylamino group having 6 to 20 carbon atoms and an alkylidene group having 1 to 20 carbon atoms, R, $R^1$ to $R^{11}$, $X^1$ and $X^2$ are each independently unsubstituted or substituted with one or more substituents selected from the group consisting of a halogen group, an alkyl group having 1 to 20 carbon atoms, a haloalkyl group having 1 to 20 carbon atoms, an alkenyl group having 2 to 20 carbon atoms, an alkoxy group having 1 to 20 carbon atoms, a cycloalkyl group having 3 to 20 carbon atoms, an aryl group having 6 to 20 carbon atoms, an arylalkyl group having 7 to 20 carbon atoms, an alkylaryl group having 7 to 20 carbon atoms and an aryloxy group having 6 to 20 carbon atoms, and n is an integer of 1 or 2, and when n is an integer of 2, two $R^{11}$s are the same as or different from each other.

Another embodiment of the present disclosure provides a catalyst composition including the transition metal compound of Chemical Formula 1.

Still another embodiment of the present disclosure provides an olefin-based polymer prepared using the catalyst composition, having density of 0.866 g/cc or less, and having a crystallization temperature peak at 40° C. or lower and a melting temperature peak at 60° C. or lower when measured using a differential scanning calorimeter.

Yet another embodiment of the present disclosure provides a ligand compound of the following Chemical Formula 2 useful in preparing the transition metal compound of Chemical Formula 1.

[Chemical Formula 2]

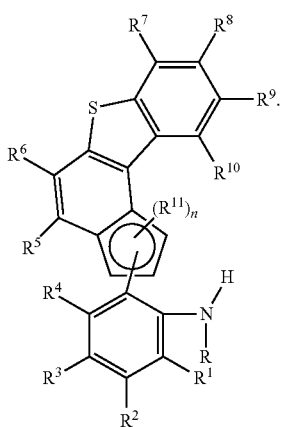

In Chemical Formula 2, R, $R^1$ to $R^{11}$, and n have the same definitions as above.

Advantageous Effects

A transition metal compound according to the present disclosure includes an amino group linked to a phenylene bridge in a ring form and maintains a rigid pentagonal ring structure with the transition metal, and therefore, is capable of exhibiting excellent structural stability together with excellent polymerization reactivity. As a result, the transition metal compound is useful for olefin-based polymers, particularly, low density polyethylene, and is useful in preparing a copolymer of ethylene and alpha-olefin since approaches of monomers having large steric hindrance are more facilitated structurally.

MODE FOR CARRYING OUT THE INVENTION

Hereinafter, the present disclosure will be described in more detail in order to illuminate the present disclosure.

Terms or words used in the present specification and the claims are not to be interpreted limitedly to common or dictionary meanings, and shall be interpreted as meanings and concepts corresponding to technological ideas of the present disclosure based on a principle in which inventors may suitably define the concepts of terms in order to describe their own invention in the best possible way.

In the present specification, unless particularly defined otherwise, an alkyl group means a linear or branched aliphatic saturated hydrocarbon group having 1 to 20 carbon atoms. Specifically, the alkyl group includes a linear or branched alkyl group having 1 to 20 carbon atoms and more specifically 1 to 6 carbon atoms. Specific examples of the alkyl group may include a methyl group, an ethyl group, an n-propyl group, an isopropyl group, an n-butyl group, an isobutyl group, a sec-butyl group, a t-butyl group, a pentyl group, an iso-amyl group, a hexyl group or the like.

In the present specification, unless particularly defined otherwise, an alkoxy group means a linear or branched alkyl group having 1 to 20 carbon atoms bonding with oxygen (—$OR_a$). Specifically, the alkyl group ($R_a$) includes an alkyl group having 1 to 20 carbon atoms and more specifically 1 to 6 carbon atoms. Specific examples of the alkoxy group may include a methoxy group, an ethoxy group, a propoxy group, a butoxy group, a t-butoxy group or the like.

In the present specification, unless particularly defined otherwise, an alkenyl group means a linear or branched aliphatic unsaturated hydrocarbon group having 2 to 20 carbon atoms including a carbon-carbon double bond. Specifically, the alkenyl group includes an alkenyl group having 2 to 6 carbon atoms. Specific examples of the alkenyl group may include an ethenyl group, a propenyl group, a butenyl group or the like.

In the present specification, unless particularly defined otherwise, a cycloalkyl group means a cyclic saturated hydrocarbon group having 3 to 20 carbon atoms. Specifically, the cycloalkyl group includes a cycloalkyl group having 3 to 6 carbon atoms. Specific examples of the cycloalkyl group may include a cyclopropyl group, a cyclobutyl group, a cyclohexyl group or the like.

In the present specification, unless particularly defined otherwise, an aryl group means a carbocycle aromatic radical having 6 to 20 carbon atoms including one or more rings, and the rings may be attached together using a pendant method or fused. Specifically, the aryl group includes an aryl group having 6 to 20 carbon atoms and more specifically 6 to 12 carbon atoms. Specific examples of the aryl group may include a phenyl group, a naphthyl group, a biphenyl group or the like.

In the present specification, unless particularly defined otherwise, an arylalkyl group means a functional group (Ar—$R_a$—) substituting a linear or branched alkyl group ($R_a$) with an aryl group (Ar), an aromatic hydrocarbon group. Specifically, the arylalkyl group includes an arylalkyl group having 7 to 20 carbon atoms and more specifically 7 to 12 carbon atoms. Specific examples of the arylalkyl group may include a benzyl group, a phenethyl group or the like.

In the present specification, unless particularly defined otherwise, an alkylaryl group means a functional group ($R_a$—Ar—) substituting an aromatic hydrocarbon group (Ar) with a linear or branched alkyl group ($R_a$). Specifically, the alkylaryl group includes an alkylaryl group having 7 to 20 carbon atoms and more specifically 7 to 12 carbon atoms.

In the present specification, unless particularly defined otherwise, an aryloxy group means an aryl group bonding with oxygen (—OAr), and herein, the aryl group has the same definition as above. Specifically, the aryloxy group includes an aryloxy group having 6 to 20 carbon atoms and more specifically 6 to 12 carbon atoms. Specific examples of the aryloxy group may include phenoxy or the like.

In the present specification, unless particularly defined otherwise, a silyl group means a —$SiH_3$ radical derived from silane, and at least one of hydrogen atoms in the silyl group may be substituted with various organic groups such as an alkyl group ($R_a$) or a halogen group.

In the present specification, unless particularly defined otherwise, an alkylamino group means a functional group substituting at least one of hydrogens in the amino group (—$NH_2$) with an alkyl group ($R_a$), and herein, the alkyl group ($R_a$) has the same definition as above. Specifically, the alkylamino group may be —$N(R_b)_2$ (herein, $R_b$s may each be a hydrogen atom or a linear or branched alkyl group having 1 to 20 carbon atoms, however, both $R_b$s are not hydrogen atoms at the same time).

In the present specification, unless particularly defined otherwise, an arylamino group means a functional group substituting at least one of hydrogens in the amino group (—$NH_2$) with an aryl group (Ar), and herein, the aryl group has the same definition as above.

In the present specification, unless particularly defined otherwise, an alkylidene group means a divalent aliphatic hydrocarbon group removing two hydrogen atoms from the same carbon of the alkyl group. Specifically, the alkylidene group includes an alkylidene group having 1 to 20 carbon atoms and more specifically 1 to 12 carbon atoms. Specific examples of the alkylidene group may include a propan-2-ylidene group or the like.

In the present specification, unless particularly defined otherwise, a hydrocarbyl group means a monovalent hydrocarbon group having 1 to 60 carbon atoms formed only with carbon and hydrogen regardless of its structure such as an alkyl group, an aryl group, an alkenyl group, an alkylaryl group and an arylalkyl group.

In the present specification, unless particularly defined otherwise, a metalloid radical is a metalloid radical of a group 14 (group 4A) metal substituted with a hydrocarbyl group having 1 to 20 carbon atoms. The metalloid radical is electronically unsaturated, and may perform a role of Lewis acid. The group 14 metal may include silicon (Si), germanium, tin, arsenic or the like. Specifically, the metalloid radical may include a silyl group such as a trimethylsilyl group, a triethylsilyl group, an ethyldimethylsilyl group and a methyldiethylsilyl group; a triphenylgermyl group, a trimethylgermyl group or the like.

In the present specification, unless particularly defined otherwise, 'combinations thereof' means two or more functional groups bonding through a linking group such as a single bond, a double bond (ethylene group), a triple bond (acetylene group) or a alkylene group having 1 to 20 carbon atoms (for example, a methylene group (—$CH_2$—), an ethylene group (—$CH_2CH_2$—) or the like), or two or more functional groups being fused and linked.

A transition metal compound according to one embodiment of the present disclosure has a structure of the following Chemical Formula 1:

[Chemical Formula 1]

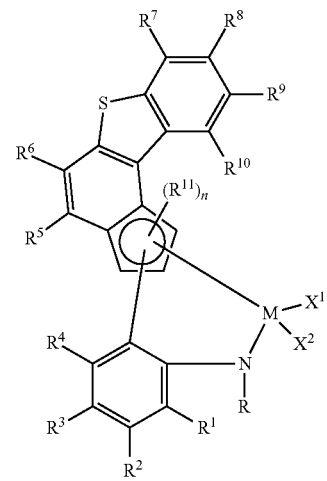

In Chemical Formula 1,

M is a group 4 transition metal,

R is selected from the group consisting of a hydrogen atom, an alkyl group having 1 to 20 carbon atoms, a cycloalkyl group having 3 to 20 carbon atoms, an aryl group having 6 to 20 carbon atoms, an arylalkyl group having 7 to 20 carbon atoms, an alkylaryl group having 7 to 20 carbon atoms and combinations thereof; or R and $R^1$ are linked to each other to form an aliphatic ring having 3 to 20 carbon atoms or an aromatic ring having 5 to 20 carbon atoms including N, $R^1$ to $R^{10}$ are each independently selected from the group consisting of a hydrogen atom, a halogen group, an alkyl group having 1 to 20 carbon atoms, an alkenyl group having 2 to 20 carbon atoms, a cycloalkyl group having 3 to 20 carbon atoms, an aryl group having 6 to 20 carbon atoms, an arylalkyl group having 7 to 20 carbon atoms, an alkylaryl group having 7 to 20 carbon atoms, an alkoxy group having 1 to 20 carbon atoms, an aryloxy group having 6 to 20 carbon atoms, a silyl group and combinations thereof, or adjacent two or more functional groups among $R^1$ to $R^{10}$ are linked to each other to form an aliphatic ring having 3 to 20 carbon atoms or an aromatic ring having 6 to 20 carbon atoms, $R^{11}$ is selected from the group consisting of an alkyl group having 1 to 20 carbon atoms, an alkenyl group having 2 to 20 carbon atoms, a cycloalkyl group having 3 to 20 carbon atoms, an aryl group having 6 to 20 carbon atoms, an arylalkyl group having 7 to 20 carbon atoms, an alkylaryl group having 7 to 20 carbon atoms, a silyl group, and a metalloid radical of a group 14 metal substituted with a hydrocarbyl group having 1 to 20 carbon atoms, $X^1$ and $X^2$ are each independently selected from the group consisting of a halogen group, an alkyl group having 1 to 20 carbon atoms, an alkenyl group having 2 to 20 carbon atoms, an aryl group having 6 to 20 carbon atoms, an alkylaryl group having 7 to 20 carbon atoms, an arylalkyl group having 7 to 20 carbon atoms, an alkylamino group having 1 to 20 carbon atoms, an arylamino group having 6 to 20 carbon atoms and an alkylidene group having 1 to 20 carbon atoms, and n is an integer of 1 or 2, and when n is an integer of 2, two $R^{11}$s are the same as or different from each other.

In addition, each functional group in Chemical Formula 1, R, $R^1$ to $R^{11}$, $X^1$ and $X^2$ may be each independently further substituted with one or more substituents selected from the group consisting of a halogen group, an alkyl group having 1 to 20 carbon atoms, a haloalkyl group having 1 to 20 carbon atoms, an alkenyl group having 2 to 20 carbon atoms, an alkoxy group having 1 to 20 carbon atoms, a cycloalkyl group having 3 to 20 carbon atoms, an aryl group having 6 to 20 carbon atoms, an arylalkyl group having 7 to 20 carbon atoms, an alkylaryl group having 7 to 20 carbon atoms and an aryloxy group having 6 to 20 carbon atoms.

In the transition metal compound of Chemical Formula 1 according to one embodiment of the present disclosure, the metal site is linked by a dibenzothiophene-fused cyclopentadienyl (hereinafter, simply referred to as 'fused Cp') ligand introducing an amino group linked to a phenylene bridge in a ring form, and structurally, the angle of the fused Cp-metal (M)-nitrogen (N) may be narrow, and the $X^1$-M-$X^2$ angle to which monomers for a polymer approach may be maintained as being wide. As a result, approaches of monomers having large steric hindrance may be more readily achieved. In addition, in the transition metal compound of Chemical Formula 1, the fused Cp, the phenylene bridge, and the nitrogen may form a more stable and rigid pentagonal ring structure with the metal site due to a ring-type bonding. In other words, the nitrogen atom of the amino group is linked by two bonds with the phenylene bridge in a ring form, and therefore, a more rigid complex compound structure may be obtained. Accordingly, when used in olefin polymerization, large quantities of alpha-olefin as well as low density polyolefin, particularly, linear low density polyethylene may be introduced, and as a result, very low density polyolefin copolymer having density of 0.866 g/cc or less may be prepared.

In addition, various substituents may be introduced to the fused Cp ring and the phenylene ring. As a result, electronic and steric environments around the metal may be controlled, and structures, physical properties and the like of the produced polyolefin may be readily controlled. Accordingly, the transition metal compound of Chemical Formula 1 may be useful as a catalyst for preparing an olefin-based polymer, however, the use is not limited thereto, and the transition metal compound is capable of being used in all usable fields.

More specifically, in Chemical Formula 1, M may be selected from the group consisting of titanium (Ti), zirconium (Zr) and hafnium (Hf), and more specifically, may be titanium (Ti).

In addition, in Chemical Formula 1, R may be more specifically selected from the group consisting of a hydrogen atom, an alkyl group having 1 to 12 carbon atoms, a cycloalkyl group having 3 to 12 carbon atoms, an aryl group having 6 to 12 carbon atoms, an arylalkyl group having 7 to 12 carbon atoms, an alkylaryl group having 7 to 12 carbon atoms and combinations thereof; or R and $R^1$ may be linked to each other to form an aliphatic ring having 4 to 10 carbon atoms or an aromatic ring having 5 to 10 carbon atoms including N, and these functional groups may be independently unsubstituted or substituted with one or more substituents selected from the group consisting of a halogen group, an alkyl group having 1 to 10 carbon atoms, a haloalkyl group having 1 to 10 carbon atoms, an alkenyl group having 2 to 10 carbon atoms, an alkoxy group having 1 to 10 carbon atoms, a cycloalkyl group having 3 to 12 carbon atoms, an aryl group having 6 to 12 carbon atoms, an arylalkyl group having 7 to 12 carbon atoms, an alkylaryl group having 7 to 12 carbon atoms and an aryloxy group having 6 to 12 carbon atoms. More specifically, R may be a hydrogen atom, an alkyl group having 1 to 6 carbon atoms or an aryl group having 6 to 12 carbon atoms; or R and $R^1$ may be linked to other to form an aliphatic ring having 4 to 6 carbon atoms including N, and these functional groups may be unsubstituted or substituted with one or more substituents selected from the group consisting of a halogen group, an alkyl group having 1 to 10 carbon atoms and a haloalkyl group having 1 to 10 carbon atoms.

More specifically, in Chemical Formula 1, $R^1$ to $R^{10}$ are each independently selected from the group consisting of a hydrogen atom, a halogen group, an alkyl group having 1 to 12 carbon atoms, an alkenyl group having 2 to 12 carbon atoms, a cycloalkyl group having 3 to 12 carbon atoms, an aryl group having 6 to 12 carbon atoms, an arylalkyl group having 7 to 12 carbon atoms, an alkylaryl group having 7 to 12 carbon atoms, an alkoxy group having 1 to 12 carbon atoms, an aryloxy group having 6 to 12 carbon atoms and a silyl group, or adjacent two or more functional groups among $R^1$ to $R^{10}$ may be linked to each other to form an aliphatic ring having 4 to 10 carbon atoms or an aromatic ring having 6 to 10 carbon atoms, and more specifically, $R^1$ to $R^{10}$ are each independently selected from the group consisting of a hydrogen atom, an alkyl group having 1 to 6 carbon atoms, an alkenyl group having 2 to 6 carbon atoms, a cycloalkyl group having 3 to 6 carbon atoms, an aryl group having 6 to 12 carbon atoms, an arylalkyl group having 7 to 12 carbon atoms and an alkylaryl group having 7 to 12 carbon atoms, or adjacent two or more functional groups among $R^1$ to $R^{10}$ may be linked to each other to form an aliphatic ring having 4 to 6 carbon atoms or an aromatic ring having 6 to 8 carbon atoms.

In addition, in Chemical Formula 1, R may be selected from the group consisting of an alkyl group having 1 to 12 carbon atoms, an alkenyl group having 2 to 12 carbon atoms, a cycloalkyl group having 3 to 12 carbon atoms, an aryl group having 6 to 12 carbon atoms, an arylalkyl group having 7 to 12 carbon atoms, an alkylaryl group having 7 to 12 carbon atoms, a silyl group, and a metalloid radical of a group 14 metal substituted with a hydrocarbyl group having 1 to 12 carbon atoms, and more specifically, $R^{11}$ may be an alkyl group having 1 to 6 carbon atoms.

In addition, in Chemical Formula 1, $X^1$ and $X^2$ may be each independently selected from the group consisting of a halogen group, an alkyl group having 1 to 6 carbon atoms, an alkenyl group having 2 to 6 carbon atoms, an aryl group having 6 to 12 carbon atoms, an alkylaryl group having 7 to 12 carbon atoms, an arylalkyl group having 7 to 12 carbon atoms, an alkylamino group having 1 to 6 carbon atoms, an arylamino group having 6 to 12 carbon atoms and an alkylidene group having 1 to 12 carbon atoms. More specifically, $X^1$ and $X^2$ may be each independently an alkyl group having 1 to 6 carbon atoms, and even more specifically a methyl group or an ethyl group.

As compounds favored for controlling electronic and steric environments around the metal (M) in Chemical Formula 1, compounds represented by the following Chemical Formulae 1a to 1c may be more specifically included:

[Chemical Formula 1a]

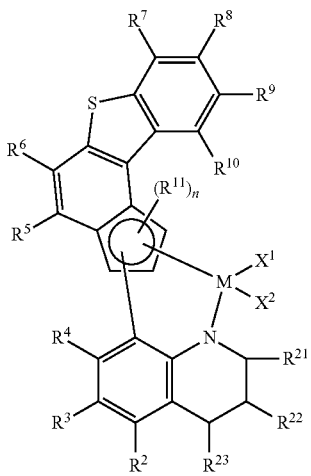

[Chemical Formula 1b]

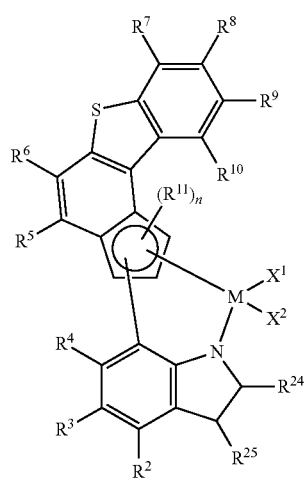

[Chemical Formula 1c]

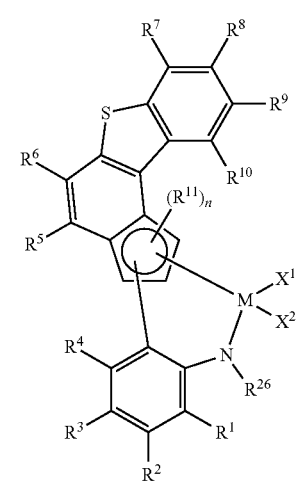

In Chemical Formulae 1a to 1c, M, $R^1$ to $R^{11}$, $X^1$, $X^2$ and n have the same definitions as above, $R^{21}$ to $R^{25}$ may be each independently selected from the group consisting of a hydrogen atom, a halogen group, an alkyl group having 1 to 20 carbon atoms, a haloalkyl group having 1 to 20 carbon atoms, an alkenyl group having 2 to 20 carbon atoms, an alkoxy group having 1 to 20 carbon atoms, a cycloalkyl group having 3 to 20 carbon atoms, an aryl group having 6 to 20 carbon atoms, an arylalkyl group having 7 to 20 carbon atoms, an alkylaryl group having 7 to 20 carbon atoms, an aryloxy group having 6 to 20 carbon atoms and combinations thereof, or adjacent two or more functional groups among $R^{21}$ to $R^{25}$ may be linked to each other to form a substituted or unsubstituted aliphatic ring having 3 to 20 carbon atoms or aromatic ring having 5 to 20 carbon atoms, and $R^{26}$ may be selected from the group consisting of a hydrogen atom, an alkyl group having 1 to 20 carbon atoms, a cycloalkyl group having 3 to 20 carbon atoms, an aryl group having 6 to 20 carbon atoms, an arylalkyl group having 7 to 20 carbon atoms, an alkylaryl group having 7 to 20 carbon atoms and combinations thereof, and these functional groups may be independently unsubstituted or substituted with one or more substituents selected from the group consisting of a halogen group, an alkyl group having 1 to 10 carbon atoms, a haloalkyl group having 1 to 10 carbon atoms, an alkenyl group having 2 to 10 carbon atoms, an alkoxy group having 1 to 10 carbon atoms, a cycloalkyl group having 3 to 12 carbon atoms, an aryl group having 6 to 12 carbon atoms, an arylalkyl group having 7 to 12 carbon atoms, an alkylaryl group having 7 to 12 carbon atoms and an aryloxy group having 6 to 12 carbon atoms.

More specifically, in Chemical Formulae 1a to 1c, M may be selected from the group consisting of titanium (Ti), zirconium (Zr) and hafnium (Hf), and more specifically, may be titanium (Ti), $R^1$ to $R^{10}$ may be each independently selected from the group consisting of a hydrogen atom, an alkyl group having 1 to 6 carbon atoms, an alkenyl group having 2 to 6 carbon atoms, a cycloalkyl group having 3 to 6 carbon atoms, an aryl group having 6 to 12 carbon atoms, an arylalkyl group having 7 to 12 carbon atoms and an alkylaryl group having 7 to 12 carbon atoms, or adjacent two or more functional groups among $R^1$ to $R^{10}$ may be linked to each other to form an aliphatic ring having 4 to 6 carbon atoms or an aromatic ring having 6 to 8 carbon atoms, $R^{11}$ is an alkyl group having 1 to 6 carbon atoms when n is 1 or 2, $R^{21}$ to $R^{25}$ may be each independently selected from the group consisting of a hydrogen atom, an alkyl group having 1 to 6 carbon atoms, an alkenyl group having 2 to 6 carbon atoms, a cycloalkyl group having 3 to 6 carbon atoms, an aryl group having 6 to 12 carbon atoms, an arylalkyl group having 7 to 12 carbon atoms and an alkylaryl group having 7 to 12 carbon atoms, or adjacent two or more functional groups among $R^{21}$ to $R^{25}$ may be linked to each other to form an aliphatic ring having 4 to 6 carbon atoms or an aromatic ring having 6 to 8 carbon atoms unsubstituted or substituted with one or more substituents selected from the group consisting of a halogen group, an alkyl group having 1 to 10 carbon atoms and a haloalkyl group having 1 to 10 carbon atoms, $R^{26}$ may be selected from the group consisting of a hydrogen atom, an alkyl group having 1 to 6 carbon atoms, a cycloalkyl group having 3 to 12 carbon atoms, an aryl group having 6 to 12 carbon atoms, an arylalkyl group having 7 to 12 carbon atoms, an alkylaryl group having 7 to 12 carbon atoms and combinations thereof, and these functional groups may be unsubstituted or substituted with one or more substituents selected from the group consisting of a halogen group, an alkyl group having 1 to 10 carbon atoms and a haloalkyl group having 1 to 10 carbon atoms, $X^1$ and $X^2$ are each independently an alkyl group having 1 to 6 carbon atoms, and n is an integer of 1 or 2, and when n is an integer of 2, two $R^{11}$s are the same as or different from each other.

As compounds even more favored for controlling electronic and steric environments around the metal (M) in Chemical Formula 1, compounds represented by the following Chemical Formulae 1a-1 to 1c-1 may be included:

[Chemical Formula 1a-1]

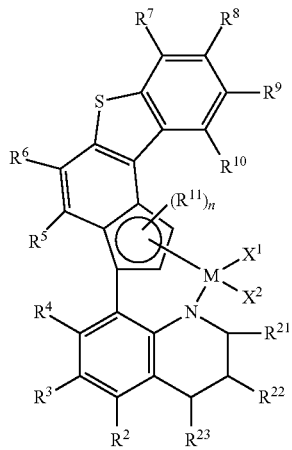

[Chemical Formula 1b-1]

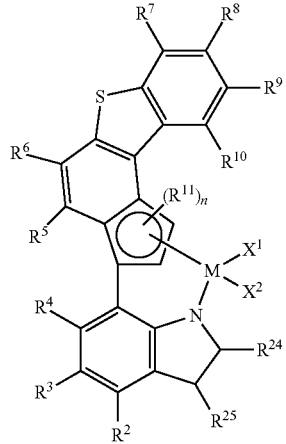

[Chemical Formula 1c-1]

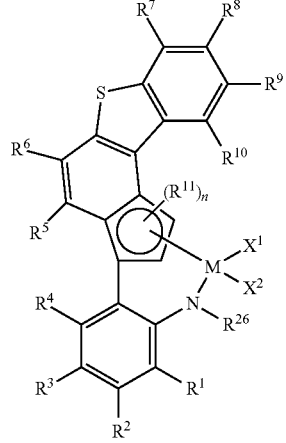

In Chemical Formulae 1a-1 to 1c-1, M, $R^1$ to $R^{11}$, $R^{21}$ to $R^{26}$, $X^1$, $X^2$ and n have the same definitions as above.

Even more specifically, the transition metal compound of Chemical Formula 1 may be selected from the group consisting of compounds of the following Chemical Formulae 1-1 to 1-12:

(1-1)

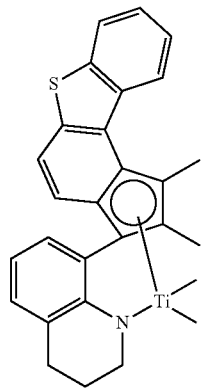

(1-2)

(1-3)

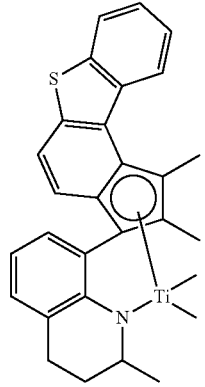

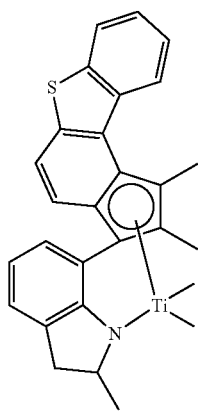
(1-4)
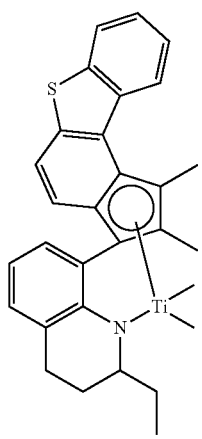
(1-5)
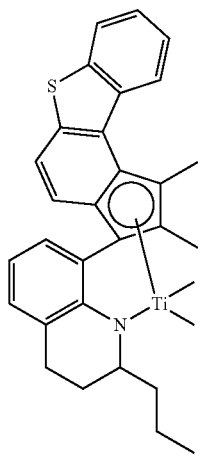
(1-6)
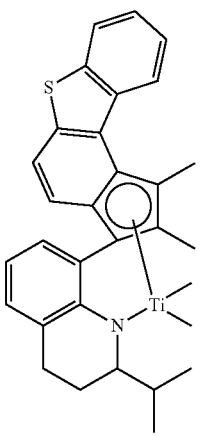
(1-7)
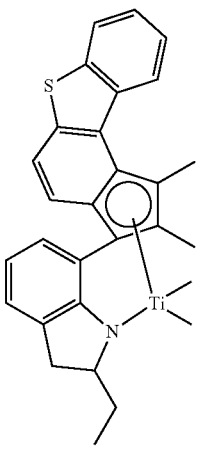
(1-8)
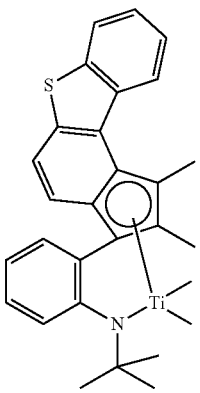
(1-9)

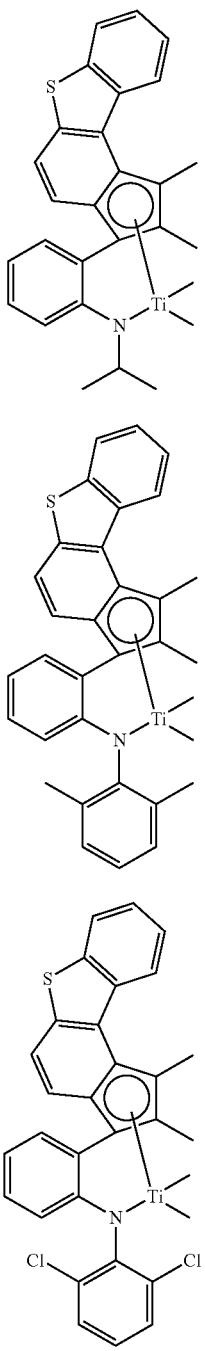

(1-10)

(1-11)

(1-12)

Meanwhile, the transition metal compound of Chemical Formula 1 having structures as above may be prepared using a preparation method including reacting a ligand compound of the following Chemical Formula 2 with an organolithium-based compound, and then reacting with a compound of the following Chemical Formula 3. Herein, an organolithium-based compound or a Grignard reagent may be selectively further added in the reaction with the compound of Chemical Formula 3. Accordingly, another embodiment of the present disclosure provides a method for preparing the transition metal compound of Chemical Formula 1.

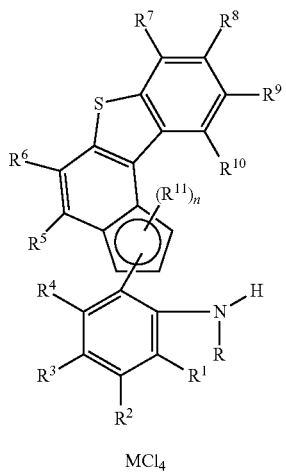

[Chemical Formula 2]

MCl$_4$   [Chemical Formula 3]

(In Chemical Formulae 2 and 3, M, R, R$^1$ to R$^{11}$, and n have the same definitions as above.)

Specifically, in preparing the transition metal compound of Chemical Formula 1 according to one embodiment of the present disclosure, the organolithium-based compound capable of being used in the reaction with the ligand compound of Chemical Formula 2 may be an alkyl lithium (R$_a$—Li, the alkyl group (R$_a$) has the same definition as above, and specifically, is a linear alkyl group having 1 to 8 carbon atoms), a cycloalkyl lithium (herein, the cycloalkyl group has the same definition as above, and specifically, is a cycloalkyl group having 3 to 12 carbon atoms), an allyl lithium, a vinyl lithium, an aryl lithium (the aryl group has the same definition as above, and specifically, is an aryl group having 6 to 12 carbon atoms), an arylalkyl lithium (the arylalkyl group has the same definition as above, and specifically, is an arylalkyl group having 7 to 12 carbon atoms) or an alkylaryl lithium (the alkylaryl group has the same definition as above, and specifically, is an arylalkyl group having 7 to 12 carbon atoms). More specifically, examples of the organolithium-based compound may include methyl lithium, ethyl lithium, isopropyl lithium, n-butyl lithium, sec-butyl lithium, t-butyl lithium, isobutyl lithium, pentyl lithium, isopentyl lithium, cyclopentyl lithium, cyclohexyl lithium, hexyl lithium, octyl lithium, allyl lithium, vinyl lithium, phenyl lithium, benzyl lithium or the like, and any one, or a mixture of two or more thereof may be used. Among these, when considering excellent reactivity with the ligand compound of Chemical Formula 2, the organolithium-based compound may be methyl lithium, n-butyl lithium, t-butyl lithium or a mixture thereof.

In addition, specific examples of the compound of Chemical Formula 3 capable of being used after the reaction between the ligand compound of Chemical Formula 2 and the organolithium-based compound may include TiCl$_4$, ZrCl$_4$ or HfCl$_4$, and any one, or a mixture of two or more thereof may be used. The compound of Chemical Formula 3 may also be used in a solvate form such as TiCl$_4$.DME (dimethyl ether). In addition, the compound of Chemical Formula 3 may be used in 1 equivalent to 1.2 equivalents with respect to 1 equivalent of the ligand compound of Chemical Formula 2.

In the reaction with the compound of Chemical Formula 3, an organolithium-based compound or a Grignard reagent may be selectively further added. In this case, the method for preparing the transition metal compound of Chemical Formula 1 according to one embodiment of the present disclosure specifically includes reacting the ligand compound of Chemical Formula 2 with an organolithium-based compound, and then reacting the resulting reactant with the compound of Chemical Formula 3, and an organolithium-based compound or a Grignard reagent. Herein, the ligand compound of Chemical Formula 2 and the organolithium-based compound are the same as described above.

In addition, the Grignard reagent may specifically be a compound of the following Chemical Formula 4.

R'MgX　　　　　　　　　　　　　　　　[Chemical Formula 4]

(In Chemical Formula 4, R' is selected from the group consisting of an alkyl group having 1 to 30 carbon atoms, an aryl group having 6 to 30 carbon atoms and an arylalkyl group having 7 to 30 carbon atoms, and X is a halogen group.)

More specifically, the Grignard reagent may be MeMgBr, EtMgCl (herein, Me is a methyl group and Et is an ethyl group) and the like, and may be used either alone as one type, or as a mixture of two or more types. In addition, the Grignard reagent may be used in 2 equivalents to 2.5 equivalents with respect to 1 equivalent of the compound of Chemical Formula 3.

The reaction of the compound of Chemical Formula 3, and a Grignard reagent or an organolithium-based compound for the reactant obtained as a result of the reaction between the compound of Chemical Formula 2 and an organolithium-based compound may be carried out at a temperature of −90° C. to 25° C. and more specifically at a temperature of −78° C. to 25° C.

From the preparation processes as above, the transition metal compound of Chemical Formula 1 having a unique structure as described above and thereby having excellent polymerization reactivity and structural stability may be prepared.

Meanwhile, the ligand compound of Chemical Formula 2 used in preparing the transition metal compound of Chemical Formula 1 according to one embodiment of the present disclosure may be prepared by reacting a compound of the following Chemical Formula 5 or an alkali metal salt thereof with an organolithium-based compound, and then reacting the result with a compound of the following Chemical Formula 6.

[Chemical Formula 5]

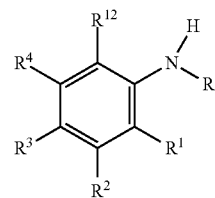

[Chemical Formula 6]

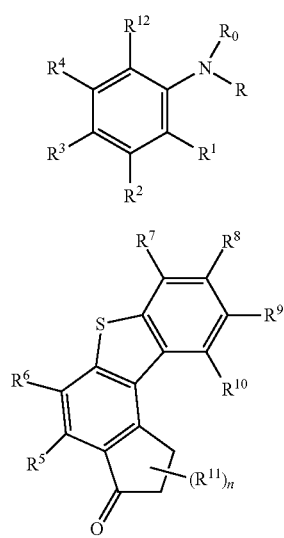

(In Chemical Formulae 5 and 6, R, $R^1$ to $R^{11}$, and n are the same as described above, $R_0$ is, as a protective group of nitrogen atom, selected from the group consisting of an alkylsilyl group such as a trimethylsilyl group; an arylalkyl group such as a benzyl group; an alkoxycarbonyl group such as a t-butoxycarbonyl group; an aryloxycarbonyl group such as a benzyloxy carbonyl group; and C(=O)O⁻, and $R^{12}$ may be a hydrogen atom.)

The compound of Chemical Formula 5 capable of being used in preparing the ligand compound of Chemical Formula 2 may be commercially purchased, or prepared using common methods. Specifically, the compound of Chemical Formula 5 may be prepared by reacting an amine-based compound of the following Chemical Formula 7 and an organolithium-based compound, then adding a compound including a protective group thereto, and reacting the result. Herein, the organolithium-based compound is the same as described above.

[Chemical Formula 7]

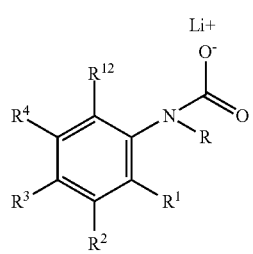

(In Chemical Formula 7, R, $R^1$ to $R^4$, and $R^{12}$ are the same as defined above.)

The compound of Chemical Formula 7 may be commercially purchased, or prepared using common methods.

In addition, examples of the compound including a protective group capable of being used in preparing the compound of Chemical Formula 5 may include trimethylsilyl chloride, benzyl chloride, t-butoxycarbonyl chloride, benzyloxycarbonyl chloride, carbon dioxide or the like, and one type, or a mixture of two or more types thereof may be used.

Specifically, when the compound including a protective group is carbon dioxide, the compound of Chemical Formula 5 may be a lithium carbamate compound of the following Chemical Formula 5a:

[Chemical Formula 5a]

(In Chemical Formula 5a, R, $R^1$ to $R^4$, and $R^{12}$ are the same as defined above.)

In addition, the compound of Chemical Formula 6 capable of being used in preparing the ligand compound of Chemical Formula 2 by being reacted with the reactant of the compound of Chemical Formula 5 and an organolithium-based compound may be prepared by mixing dibenzothiophene with a metal halide such as AlCl₃; and an acid halide such as tigloyl chloride, benzoyl chloride, hexanoyl chloride and butyryl chloride in a nonpolar solvent such as methylene chloride, and then reacting the result at −90° C. to 25° C. Herein, for the reactant obtained as a result of the reaction, an extraction process using methylene chloride, $K_2CO_3$ and the like may be further carried out.

More specifically, the ligand compound of Chemical Formula 2 may be prepared by reacting the compound of Chemical Formula 5 and an organolithium-based compound in an organic solvent such as diethyl ether, and reacting the compound obtained as a result with the compound of Chemical Formula 6 in a nonpolar solvent such as n-hexane. Herein, the compound of Chemical Formula 5, the organolithium-based compound and the compound of Chemical Formula 6 may be used in proper content considering a stoichiometric reaction ratio.

In addition, the reaction for preparing the ligand compound of Chemical Formula 2 may be carried out under a temperature of −80° C. to 50° C.

Through the reactions as above, the ligand compound of Chemical Formula 2 useful in preparing the transition metal compound according to one embodiment of the present disclosure may be prepared.

Another embodiment of the present disclosure provides a catalyst composition including the transition metal compound.

Specifically, the catalyst composition includes the transition metal compound of Chemical Formula 1, and selectively, may further include a co-catalyst preferably functioning as a counter ion, that is, an anion having weak bonding strength while cationizing the central metal by extracting $X_1$ and $X_2$ ligands in the transition metal complex so that the transition metal compound of Chemical Formula 1 becomes an active catalyst component used in preparing an ethylene homopolymer or a copolymer of ethylene and α-olefin.

The co-catalyst may be used without particular limit as long as it is known in the art such as alkyl aluminoxane, alkyl aluminum or Lewis acid. Specifically, the co-catalyst may include any one or a mixture of two or more selected from the group consisting of compounds of the following Chemical Formulae 8 to 11:

—[Al($R^{31}$)—O]$_a$—     [Chemical Formula 8]

A($R^{32}$)$_3$     [Chemical Formula 9]

[L-H]$^+$[W(D)$_4$]$^-$     [Chemical Formula 10]

[L]$^+$[W(D)$_4$]$^-$     [Chemical Formula 11]

In Chemical Formulae 8 to 11, $R^{31}$ and $R^{32}$ are each independently selected from the group consisting of a halogen group, a hydrocarbyl group having 1 to 20 carbon atoms, and a hydrocarbyl group having 1 to 20 carbon atoms substituted with a halogen group, A is aluminum or boron, Ds are each independently an aryl group having 6 to 20 carbon atoms or an alkyl group having 1 to 20 carbon atoms in which one or more hydrogen atoms may be substituted with a substituent, and herein, the substituent is at least any one selected from the group consisting of a halogen group, a hydrocarbyl group having 1 to 20 carbon atoms, an alkoxy group having 1 to 20 carbon atoms and an aryloxy group having 6 to 20 carbon atoms, H is a hydrogen atom, L is a neutral or cationic Lewis acid, W is a group 13 element, and a is an integer of 2 or greater.

In the co-catalyst, the compounds of Chemical Formulae 8 and 9 function as an alkylating agent for the transition metal compound, and the compounds of Chemical Formulae 10 and 11 function as an activating agent for the transition metal compound or the alkylated transition metal compound.

More specifically, the compound of Chemical Formula 8 may be an alkyl aluminoxane, and herein, the alkyl group is as described above. Even more specifically, the compound of Chemical Formula 8 may include methyl aluminoxane, ethyl aluminoxane, isobutyl aluminoxane, butyl aluminoxane or the like, and any one, or a mixture of two or more thereof may be used. Even more specifically, the compound of Chemical Formula 8 may be methyl aluminoxane.

In addition, the compound of Chemical Formula 9 may be more specifically an alkyl aluminum or an alkyl boron, and herein, the alkyl group is as described above. Even more specifically, the compound of Chemical Formula 9 may include trimethyl aluminum, triethyl aluminum, triisobutyl aluminum, tripropyl aluminum, tributyl aluminum, dimethyl chloroaluminum, triisopropyl aluminum, tri-s-butyl aluminum, tricyclopentyl aluminum, tripentyl aluminum, triisopentyl aluminum, trihexyl aluminum, trioctyl aluminum, ethyldimethyl aluminum, methyldiethyl aluminum, triphenyl aluminum, tri-p-tolyl aluminum, dimethyl aluminum methoxide, dimethyl aluminum ethoxide, trimethyl boron, triethyl boron, triisobutyl boron, tripropyl boron, tributyl boron or the like, and any one, or a mixture of two or more thereof may be used. Even more specifically, the compound of Chemical Formula 9 may be trimethyl aluminum, triethyl aluminum or triisobutyl aluminum.

In addition, the compounds of Chemical Formulae 10 and 11 include a non-coordinative bonding anion compatible a cation, a BrØnsted acid, and herein, the anion may contain a single coordinate bonding complex compound having a relatively large size and including metalloids. More specifically, the compounds of Chemical Formulae 10 and 11 may be a salt containing an anion including a coordinate bonding complex compound containing a single boron atom in the anion part.

Specific examples of such compounds may include trialkyl ammonium salts such as trimethyl ammonium tetrakis(pentafluorophenyl)borate, triethyl ammonium tetrakis(pentafluorophenyl)borate, tripropyl ammonium tetrakis(pentafluorophenyl)borate, tri(n-butyl)ammonium tetrakis(pentafluorophenyl)borate, tri(2-butyl)ammonium tetrakis(pentafluorophenyl)borate, N,N-dimethyl anilinium tetrakis(pentafluorophenyl)borate, N,N-dimethyl anilinium n-butyltris(pentafluorophenyl)borate, N,N-dimethyl anilinium benzyltris(pentafluorophenyl)borate, N,N-dimethyl anilinium tetrakis(4-(t-butyldimethylsilyl)-2,3,5,6-tetrafluorophenyl)borate, N,N-dimethyl anilinium tetrakis(4-triisopropylsilyl)-2,3,5,6-tetrafluorophenyl)borate, N,N-dimethyl anilinium pentafluorophenoxy tris (pentafluorophenyl)borate, N,N-diethyl anilinium tetrakis(pentafluorophenyl)borate, N,N-dimethyl-2,4,6-trimethyl anilinium tetrakis(pentafluorophenyl)borate, trimethyl ammonium tetrakis(2,3,4,6-tetrafluorophenyl)borate, triethyl ammonium tetrakis(2,3,4,6-tetrafluorophenyl)borate, tripropyl ammonium tetrakis(2,3,4,6-tetrafluorophenyl)borate, tri(n-butyl)ammonium tetrakis(2,3,4,6-tetrafluorophenyl)borate, dimethyl(t-butyl)ammonium tetrakis(2,3,4,6-tetrafluorophenyl)borate, N,N-dimethyl anilinium tetrakis(2,3,4,6-tetrafluorophenyl)borate, N,N-diethylanilinium tetrakis (2,3,4,6-tetrafluorophenyl)borate, N,N-dimethyl-2,4,6-trimethyl anilinium tetrakis(2,3,4,6-tetrafluorophenyl)borate, decyldimethyl ammonium tetrakis (pentafluorophenyl)borate, dodecyldimethyl ammonium tetrakis(pentafluorophenyl)borate, tetradecyldimethyl ammonium tetrakis(pentafluorophenyl)borate, hexadecyldimethyl ammonium tetrakis(pentafluorophenyl)borate, octadecyldimethyl ammonium tetrakis(pentafluorophenyl)borate, eicosyldimethyl ammonium tetrakis(pentafluorophenyl)borate, methyldidecyl ammonium tetrakis(pentafluorophenyl)borate, methyldidodecyl ammonium tetrakis(pentafluorophenyl)borate, methylditetradecyl ammonium tetrakis(pentafluorophenyl)borate, methyldihexadecyl ammonium tetrakis(pentafluorophenyl)borate, methyldioctadecyl ammonium tetrakis(pentafluorophenyl)borate, methyldieicosyl ammonium tetrakis(pentafluorophenyl)borate, tridecyl ammonium tetrakis(pentafluorophenyl)borate, tridodecyl ammonium tetrakis(pentafluorophenyl)borate, tritetradecyl ammonium tetrakis(pentafluorophenyl)borate, trihexadecyl ammonium tetrakis(pentafluorophenyl)borate, trioctadecyl ammonium tetrakis(pentafluorophenyl)borate, trieicosyl ammonium tetrakis(pentafluorophenyl)borate, decyldi(n-butyl)ammonium tetrakis(pentafluorophenyl)borate, dodecyldi(n-butyl)ammonium tetrakis(pentafluorophenyl)borate, octadecyldi(n-butyl)ammonium tetrakis(pentafluorophenyl)borate, N,N-didodecyl anilinium tetrakis(pentafluorophenyl)borate, N-methyl-N-dodecyl anilinium tetrakis(pentafluorophenyl)borate or methyldi(dodecyl)ammonium tetrakis(pentafluorophenyl)borate; dialkyl ammonium salts such as di-(i-propyl) ammonium tetrakis(pentafluorophenyl)borate or dicyclohexyl ammonium tetrakis(pentafluorophenyl)borate; carbonium salts such as tropylium tetrakis(pentafluorophenyl)borate, triphenyl methylium tetrakis(pentafluorophenyl)borate or benzene(diazonium) tetrakis(pentafluorophenyl)borate, or the like, and any one, or a mixture of two or more thereof may be used. Even more specifically, the compounds of Chemical Formulae 10 and 11 may include N,N-dimethyl anilinium tetrakis(pentafluorophenyl)borate, tributyl ammonium tetrakis(pentafluorophenyl)borate, di(octadecyl)methyl ammonium tetrakis(pentafluorophenyl)borate, di(octadecyl)(n-butyl) ammonium tetrakis(pentafluorophenyl)borate, triphenyl methylium tetrakis(pentafluorophenyl)borate, tropylium tetrakis(pentafluorophenyl)borate, or the like.

The transition metal compound of Chemical Formula 1 and the co-catalyst may be used in a form impregnated in a carrier, and herein, an inorganic carrier such as silica or alumina may be used as the carrier. Using in a form impregnated in an inorganic carrier as above may be useful for slurry polymerization or gas-phase polymerization in the polymerization for preparing an olefin-based polymer thereafter.

The catalyst composition having compositions as above may be prepared using common methods, and specifically, may be prepared using a preparation method (first method) including obtaining a mixture by bringing the transition metal compound of Chemical Formula 1 into contact with the alkylating agent of Chemical Formula 8 or 9, and adding the activating agent of Chemical Formula 10 or 11 to the mixture, or may be prepared using a preparation method (second method) including bringing the transition metal compound of Chemical Formula 1 into contact with the activating agent of Chemical Formula 10 or 11.

In the first method, a molar ratio of the alkylating agent of Chemical Formula 8 or 9 with respect to the transition metal compound of Chemical Formula 1 may be 1:2 to 5,000, more specifically, 1:10 to 1,000, and even more specifically 1:20 to 500. In addition, a molar ratio of the activating agent of Chemical Formula 10 or 11 with respect to the transition metal compound of Chemical Formula 1 may be 1:1 to 25, more specifically 1:1 to 10, and even more specifically 1:1 to 5. When a molar ratio of the alkylating agent of Chemical Formula 8 or 9 with respect to the transition metal compound of Chemical Formula 1 is less than 1:2, the amount of the alkylating agent is excessively small, which may lead to concern of transition metal compound alkylation not being sufficiently progressed, and when the molar ratio is greater than 1:5,000, activation of the alkylated transition metal compound may be difficult due to a side reaction between the excess alkylating agent and the activating agent of Chemical Formula 10 or 11 added afterward. In addition, when a molar ratio of the activating agent of Chemical Formula 10 or 11 with respect to the transition metal compound of Chemical Formula 1 is less than 1:1, the amount of the alkylating agent is relatively small causing insufficient activation of the transition metal compound, which may lead to concern of reducing activity of the produced catalyst composition, and the molar ratio being greater than 1:25 may cause concern of cost increases in preparing the catalyst composition due to excessive use of the activating agent, and decline in the purity of the produced polymer.

In the second method, a molar ratio of the activating agent of Chemical Formula 10 or 11 with respect to the transition metal compound of Chemical Formula 1 may be 1:1 to 500, more specifically 1:1 to 50, and even more specifically 1:2 to 25. When the molar ratio is less than 1:1, the amount of the alkylating agent is relatively small causing incomplete activation of the transition metal compound, which may lead to concern of reducing activity of the produced catalyst composition, and the molar ratio being greater than 1:500 may cause concern of cost increases in preparing the catalyst composition due excessive use of the activating agent, and decline in the purity of the produced polymer.

In addition, in the preparation of the catalyst composition, aliphatic hydrocarbon-based solvents such as pentane, hexane or heptane; or aromatic-based solvents such as benzene or toluene may be used as a reaction solvent, however, the solvent is not limited thereto, and all solvents capable of being used in the art may be used.

As described above, the catalyst composition according to one embodiment of the present disclosure includes the transition metal compound of Chemical Formula 1 having excellent structural stability as well as structurally very facilitating monomer approaches, and therefore, may exhibit excellent polymerization reactivity, and particularly, may exhibit excellent reactivity for olefin monomers having large steric hindrance.

In addition, by including the co-catalyst as above together with the transition metal compound, the co-catalyst activates the transition metal compound to a proper degree and suppresses the production of excessively long polymer chains in preparing an olefin-based polymer, and meanwhile, the transition metal compound and the co-catalyst randomize bonding of olefin-based monomers, and as a result, an olefin-based polymer having low crystallization temperature and melting temperature as well as having low density may be prepared.

The catalyst composition is capable of being used in various fields, and among these, may be useful in preparing an olefin-based polymer, particularly, in preparing a low density ethylene polymer or a copolymer of ethylene and alpha-olefin.

Accordingly, another embodiment of the present disclosure provides an olefin-based polymer prepared using the catalyst composition.

The olefin-based polymer may be prepared according to common methods for preparing an olefin-based polymer except that the catalyst composition is used. Specifically, the olefin-based polymer brings the catalyst composition into contact with one or more olefin monomers for polymerization reaction, and as a result, may be prepared to an olefin-based homopolymer or copolymer. Specifically, the olefin-based polymer may be an ethylene homopolymer, or a copolymer of ethylene and α-olefin.

The polymerization for preparing the olefin-based polymer may be carried out using various methods such as slurry polymerization, liquid-phase polymerization, gas-phase polymerization or bulk polymerization, and more specifically, may be carried out through liquid-phase polymerization.

When the polymerization is carried out through liquid-phase polymerization, olefin monomers may be dissolved and diluted in a solvent for polymerization such as an aliphatic hydrocarbon solvent having 5 to 12 carbon atoms (for example, pentane, hexane, heptane, nonane, decane, isomers thereof or the like); an aromatic hydrocarbon solvent having 6 to 20 carbon atoms (for example, toluene, benzene or the like) or a chlorinated hydrocarbon-based solvent (for example, dichloromethane, chlorobenzene or the like) to be used. Herein, small amounts of water, air or the like functioning as a catalyst poison and reducing catalytic activity for the solvent for polymerization may be removed using an alkyl aluminum.

In addition, specific examples of the monomer for preparing the olefin-based polymer may include ethylene, alpha-olefin, cyclic olefin or the like, and in addition thereto, diene olefin-based monomers or triene olefin-based monomers having two or more double bonds, and the like, may also be used. More specifically, examples of the olefin-based monomer may include ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene, 1-eicosene, norbornene, norbornadiene, ethylidene norbornene, phenyl norbornene, vinyl norbornene, dicyclopentadiene, 1,4-butadiene, 1,5-pentadiene, 1,6-hexadiene, styrene, alpha-methylstyrene, divinylbenzene or 3-chloromethylstyrene, 2,3-diisoprophenylidene-5-norbornene, 2-ethylidene-3-isopropylidene-5-norbornene, 2-prophenyl-2,5-norbornadiene, 1,3,7-octatriene, 1,4,9-decatriene or the like, and any one, or a mixture of two or more thereof may be used.

In addition, when preparing a copolymer of ethylene and α-olefin as the olefin-based polymer, α-olefin having 3 to 18 carbon atoms may be used as a co-monomer together with ethylene. Specifically, examples of the α-olefin may include propylene, 1-butene, 1-pentene, 4-methyl-1-pentene, 1-hexene, 1-octene, 1-decene, 1-dodecene, 1-hexadecene, 1-octadecene or the like, and any one, or a mixture of two or more thereof may be used. More specifically, 1-butene, 1-hexene, 1-octene or 1-decene may be used.

When preparing the copolymer, the α-olefin may be used in the content to make the ethylene content in the finally prepared copolymer 50% by weight or greater, more specifically 60% by weight or greater and even more specifically from 60% by weight to 99% by weight.

In addition, a process for preparing the olefin polymer may be carried out at 20° C. to 500° C., more specifically at 25° C. to 200° C. and even more specifically at 50° C. to 100° C. Herein, the reaction pressure may be from 0.1 bar to 7 bar and more specifically from 1 bar to 5 bar.

The polymer prepared using the preparation method as above exhibits low density by using the catalyst composition including the transition metal compound of Chemical Formula 1. Specifically, the polymer may have very low density of 0.866 g/cc or less.

With the low density property described above, the polymer may have at least one or more and specifically one or two crystallization temperature (Tc) peaks when measured using a differential scanning calorimeter. Having two crystallization temperature peaks is due to a different type of copolymer being produced by the changes in the catalyst steric property caused by the catalyst compound having a chiral center. More specifically, at least one crystallization temperature may appear at 40° C. or lower, more specifically at 35° C. or lower and even more specifically at 15° C. to 35° C.

As for the melting temperature (Tm), at least one or more and specifically one or two melting temperature peaks may appear as well, and more specifically, one melting temperature peak may appear at 60° C. or lower, more specifically at 55° C. or lower and even more specifically at 30° C. to 52° C. By having lower crystallization temperature and melting temperature compared to existing olefin-based polymers, more superior processability may be obtained.

In the present disclosure, Tc and Tm may be measured using a differential scanning calorimeter (DSC) 2920 manufactured by TA Corporation, and herein, the measured values are obtained through second melt raising the temperature by 10° C. per minute in order to remove thermal history of the polymer. In the measured DSC curve, Tc is a maximum point of the exothermic peak in the cooling, and Tm is a maximum point of the endothermic peak in the second temperature raising.

In addition, the polymer may have a melt index (MI) of 50 g/min or less and more specifically 1 g/min to 30 g/min under a load of 2.16 kg. By having such a low melting index, mechanical properties such as rigidity and impact resistance are enhanced.

The olefin-based polymer having physical properties as above may be used in various fields and applications such as for automobiles, for wires, for toys, for fibers, for medicines, for constructions or for consumer goods.

Another embodiment of the present disclosure provides the ligand compound of Chemical Formula 2 useful in preparing the transition metal compound of Chemical Formula 1.

The ligand compound of Chemical Formula 2 is the same as described above.

Specifically, the ligand compound of Chemical Formula 2 may be a compound selected from the group consisting of the following Chemical Formulae 2-1 to 2-12.

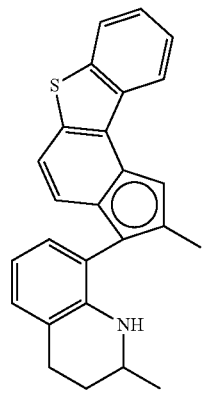

(2-1)

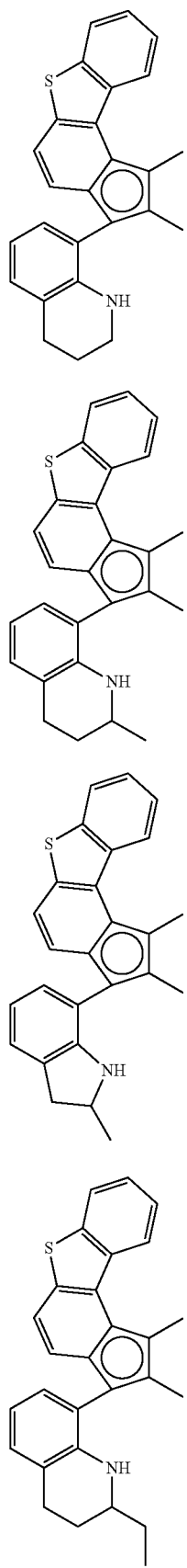
(2-2)
(2-3)
(2-4)
(2-5)
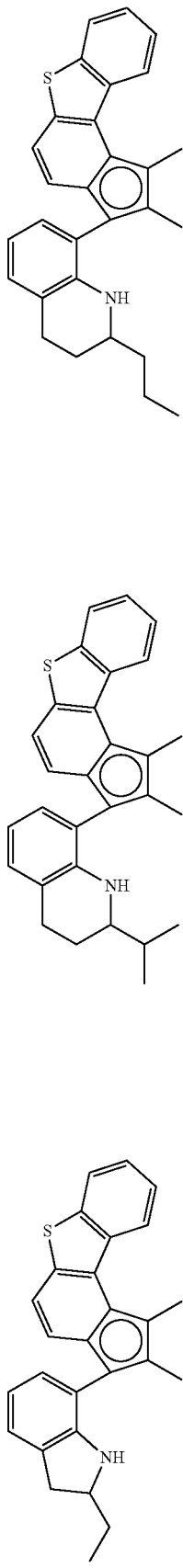
(2-6)
(2-7)
(2-8)

(2-9)
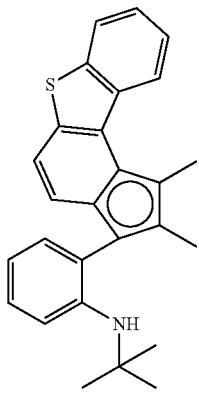

(2-10)
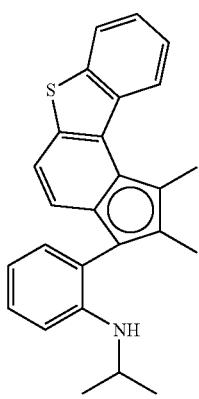

(2-11)
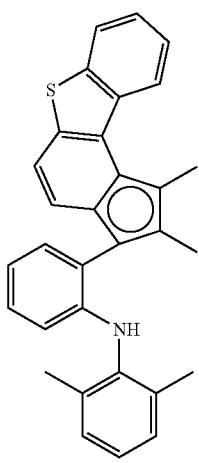

(2-12)
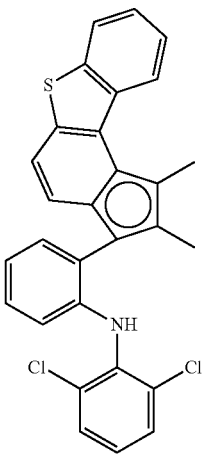

The ligand compound of Chemical Formula 2 according to one embodiment of the present disclosure includes a linking structure of a dibenzothiophene-fused cyclopentadienyl group and a phenylene group introducing an amino group into the molecule, and therefore, is capable of enhancing structural stability of the transition metal compound by forming a rigid pentagonal ring when forming coordinate bonds with the metal, and is capable of enhancing thermal stability of a catalyst due to high electron density around the transition metal, and in addition thereto, is capable of preparing a high molecular weight and yet linear low density copolymer since monomer approaches are readily achieved structurally in the copolymerization of ethylene and monomers having large steric hindrance.

The ligand compound of Chemical Formula 2 is an intermediate obtained when preparing the transition metal compound of Chemical Formula 1, but may also be used in other applications.

Hereinafter, examples of the present disclosure will be described in detail so that those skilled in the art may readily carry out the present disclosure. However, the present disclosure may be implemented in many different forms, and is not limited to the examples described herein.

Preparation of Ketone Compound (A)

10 g of dibenzothiophene was dissolved in 50 ml of methylene chloride (MC) in a Schlenk flask. 9.8 g of $AlCl_3$, 60 ml of MC, and methacryloyl chloride were stirred in another Schlenk flask, and the dibenzothiophene solution dissolved in MC previously was slowly added thereto at −78° C., and reacted. After reacting overnight, the reaction solution was transferred to 0° C. ice water via a cannula, and then the resulting reactant was extracted with MC and a supersaturated $K_2CO_3$ solution to obtain a ketone-based compound (A) of the following structure.

(A)
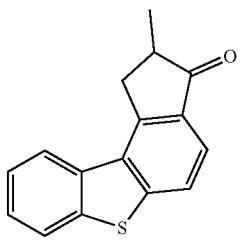

1H-NMR (500 MHz, CDCl$_3$): 8.22, 7.80, 7.45 (6H), 3.94 (1H), 3.22, 2.84 (2H), 1.37 (3H)

Preparation of Ketone Compound (B)

10 g of dibenzothiophene was dissolved in 50 ml of methylene chloride (MC) in a Schlenk flask. 9.8 g of AlCl$_3$, 60 ml of MC, and tigloyl chloride were stirred in another Schlenk flask, and the dibenzothiophene solution dissolved in MC previously was slowly added thereto at −78° C., and reacted. After reacting overnight, the reaction solution was transferred to 0° C. ice water via a cannula, and then the resulting reactant was extracted with MC and a supersaturated K$_2$CO$_3$ solution to obtain a ketone-based compound (B) of the following structure.

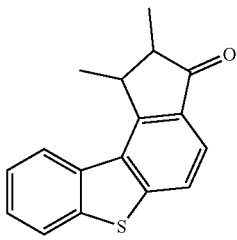

(B)

1H-NMR (500 MHz, CDCl$_3$): 8.29 (1H), 7.93 (1H), 7.85 (2H), 7.54 (2H), 4.27 (1H), 1.04 (1H), 1.37 (6H)

Preparation Example 1-1: Preparation of Ligand

To a solution dissolving 1,2,3,4-tetrahydroquinoline (5 mmol) in 8 ml of methyl-tert-butyl ether (MTBE), n-BuLi (2.3 ml, 2.5 M in hexane) was slowly added dropwise at −20° C. After slowly raising the temperature to room temperature (20±5° C.), the result was stirred for 4 hours at room temperature. The temperature was lowered to −78° C., and the result was stirred for 1 hour while injecting CO$_2$ (g) thereto. After slowly raising the temperature, the result was stirred for 12 hours at room temperature while removing residual CO$_2$ (g). After injecting THF (0.53 ml) and t-BuLi (3.82 ml) thereto at −20° C., the result was low temperature ripened for 2 hours at −20° C. Ketone A (0.694 g, 0.55 eq.) was dissolved in a tetrahydrofuran (THF) solution (0.6 M) and slowly added dropwise thereto. After stirring the result for 12 hours at room temperature, 1.0 ml of water was injected thereto, then hydrochloric acid (6 N, 30 ml) was introduced thereto, and the result was stirred for 30 minutes to progress with an elimination reaction. The obtained mixture was extracted with MC, then neutralized with triethanolamine (TEA) and an aqueous NaHCO$_3$ solution, and after taking the organic solvent, moisture was removed using MgSO$_4$. A ligand (2-1) of the following structure was obtained in a 260 mg solid form through a silica-gel column (obtained amount=346 mg, yield=33%).

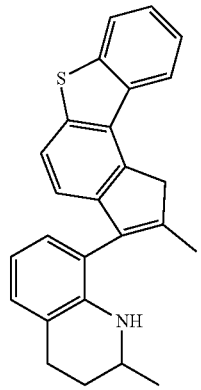

(2-1)

$^1$H NMR (CDCl$_3$): 8.25 (d, 1H), 7.89 (d, 1H), 7.72 (t, 1H), 7.5 (m, 2H), 7.23 (m, 1H), 7.03 (d, 1H), 6.98 (m, 1H), 6.69 (q, 1H), 3.4 (m, 1H), 2.9 (m, 1H+1H), 2.19 (d, 3H), 1.94 (m, 1H), 164 (m, 1H), 1.07 (m, 3H)

Preparation Example 1-2: Preparation of Ligand

To a solution dissolving 1,2,3,4-tetrahydroquinoline (1 g, 7.51 mmol) in 12 ml of methyl-tert-butyl ether (MTBE), n-BuLi (8.63 ml, 1.15 eq.) was slowly added dropwise at −20° C. After slowly raising the temperature to room temperature, the result was stirred for 4 hours at room temperature. The temperature was lowered to −78° C., and the result was stirred for 1 hour while injecting CO$_2$ (g) thereto. After slowly raising the temperature, the result was stirred for 12 hours at room temperature while removing residual CO$_2$ (g). After injecting THF (9.76 mmol, 0.8 ml) and t-BuLi (9.76 mmol, 1.3 eq.) thereto at −20° C., the result was low temperature ripened for 2 hours at −20° C. Ketone B (1.2 g, 4.5 mmol) was dissolved in a THF solution (0.5 M) and slowly added dropwise thereto. After stirring the result for 12 hours at room temperature, 1.0 ml of water was injected thereto, then hydrochloric acid (6 N, 30 ml) was introduced thereto, and the result was stirred for 30 minutes to progress with an elimination reaction. The obtained mixture was extracted with MC, then neutralized with TEA and an aqueous NaHCO$_3$ solution, and after taking the organic solvent, moisture was removed using MgSO$_4$. A 8-(1,2-dimethyl-1H-benzo[b]indeno[4,5-d]thiophen-3-yl)-1,2,3,4-tetrahydroquinoline ligand (2-2) in a bright yellow solid form was obtained through a silica-gel column (obtained amount=203 mg, yield=12%).

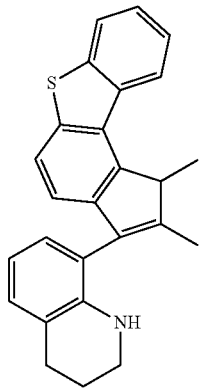

(2-2)

$^1$H NMR (CDCl$_3$): δ 1.59 (dd, 3H, Cp-CH$_3$), 1.97 (m, 2H, THQ-CH$_2$), 2.18 (d, 3H, Cp-CH$_3$), 2.88 (m, 2H, THQ-CH$_2$), 3.22~3.24 (m, 1H, Cp-H), 3.28 (t, 1H THQ-CH$_2$), 3.77~3.82 (br d, 1H, NH), 4.07 (td, 1H, THQ-CH$_2$), 6.69 (td, 1H aromatic), 6.96 (dd, 1H, aromatic), 7.02 (d, 1H, aromatic), 7.18 (dd, 1H, aromatic) 7.45~7.53 (m, 2H, aromatic), 7.70 (d, 1H, aromatic), 7.89 (d, 1H, aromatic), 8.32 (d 1H, aromatic) ppm Preparation Example 1-3: Preparation of Ligand To a solution dissolving 2-methyl-1,2,3,4-tetrahydroquinoline (1 g, 6.79 mmol) in 11 ml of methyl-tert-butyl ether (MTBE), n-BuLi (7.81 ml, 1.15 eq.) was slowly added dropwise at −20° C. After slowly raising the temperature to room temperature, the result was stirred for 4 hours at room temperature. The temperature was lowered to −78° C., and the result was stirred for 1 hour while injecting CO$_2$ (g) thereto. After slowly raising the temperature, the result was stirred for 12 hours at room temperature while removing residual CO$_2$ (g). After injecting THF (8.83 mmol, 0.7 ml) and t-BuLi (8.83 mmol, 1.3 eq.) thereto at −20° C., the result was low temperature ripened for 2 hours at −20° C. Ketone B (1.09 g, 4.1 mmol) was dissolved in a THF solution (0.5 M) and slowly added dropwise thereto. After stirring the result for 12 hours at room temperature, 0.9 ml of water was injected thereto, then hydrochloric acid (6 N, 30 ml) was introduced thereto, and the result was stirred for 30 minutes to progress with an elimination reaction. The obtained mixture was extracted with MC, then neutralized with TEA and an aqueous NaHCO$_3$ solution, and after taking the organic solvent, moisture was removed using MgSO$_4$. A 8-(1,2-dimethyl-1H-benzo[b]indeno[4,5-d]thiophen-3-yl)-2-methyl-1,2,3,4-tetrahydroquinoline ligand (2-3) in a bright yellow solid form was obtained through a silica-gel column (obtained amount=358.7 mg, yield=22%).

(2-3)

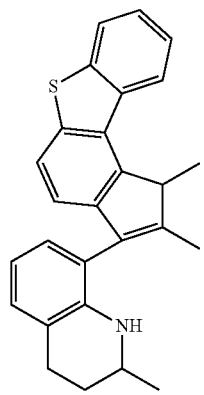

$^1$H NMR (CDCl$_3$) δ 1.04-1.10 (m, 3H, Cp-CH$_3$), 1.55~1.61 (m, 3H, 2-Me-THQ-CH$_3$), 1.60~1.67 (m, 1H, 2-Me-THQ-CH$_2$), 1.90~1.95 (m, 1H, Cp-H), 2.07 (m, 3H, Cp-CH$_3$), 2.80~3.00 (m, 2H, 2-Me-THQ-CH$_2$), 3.34~3.43 (m, 1H, 2-Me-THQ), 3.64~3.76 (m, 1H, NH), 4.07 (sextet, 1H, 2-Me-THQ-CH), 6.67~6.71 (m, 1H, aromatic), 6.97 (t, 1H, aromatic), 7.03 (d, 1H, aromatic), 7.20 (t, 1H, aromatic), 7.45~7.53 (m, 2H, aromatic), 7.67~7.71 (m, 1H, aromatic), 7.89 (d, 1H, aromatic), 8.32 (d, 1H, aromatic) ppm Preparation Example 1-4: Preparation of Ligand To a solution dissolving 2-methyl-indoline (1 g, 7.51 mmol) in 12 ml of methyl-tert-butyl ether (MTBE), n-BuLi (8.63 ml, 1.15 eq.) was slowly added dropwise at −20° C. After slowly raising the temperature to room temperature, the result was stirred for 4 hours at room temperature. The temperature was lowered to −78° C., and the result was stirred for 1 hour while injecting CO$_2$ (g) thereto. After slowly raising the temperature, the result was stirred for 12 hours at room temperature while removing residual CO$_2$ (g). After injecting THF (9.76 mmol, 0.8 ml) and t-BuLi (9.76 mmol, 1.3 eq.) thereto at −20° C., the result was low temperature ripened for 2 hours at −20° C. Ketone B (1.20 g, 4.5 mmol) was dissolved in a THF solution (0.5 M) and slowly added dropwise thereto. After stirring the result for 12 hours at room temperature, 1.0 ml of water was injected thereto, then hydrochloric acid (6 N, 30 ml) was introduced thereto, and the result was stirred for 30 minutes to progress with an elimination reaction. The obtained mixture was extracted with MC, then neutralized with TEA and an aqueous NaHCO$_3$ solution, and after taking the organic solvent, moisture was removed using MgSO$_4$. A 7-(1,2-dimethyl-1H-benzo[b]indeno[4,5-d]thiophen-3-yl)-2-methylindoline ligand (2-4) in a bright yellow solid form was obtained through a silica-gel column (obtained amount=534.5 mg, yield=31%).

(2-4)

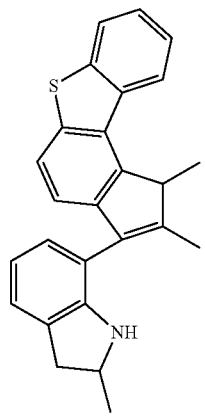

$^1$H NMR (CDCl$_3$): δ 1.25 (m, 3H, Cp-CH$_3$), 1.54~1.59 (m, 3H, 2-MI—CH$_3$), 2.11 (s, 3H, Cp-CH$_3$), 2.65~2.78 (m, 1H, 2-MI—CH$_2$), 3.15~3.28 (m, 1H, 2-MI—CH$_2$), 3.54~3.69 (br d, 1H, NH), 3.97~4.05 (m, 2H, 2-MI—CH$_2$), 6.79 (t, 1H, aromatic), 7.03 (dd, 1H, aromatic), 7.12 (t, 1H, aromatic), 7.22 (t, 1H, aromatic), 7.46~7.53 (m, 2H, aromatic), 7.70 (d, 1H, aromatic), 7.88 (d, 1H, aromatic), 8.30 (dd, 1H, aromatic) ppm Preparation Example 2-1: Preparation of Transition Metal Compound In a dry box, n-BuLi (2.05 eq.) was slowly added dropwise to the ligand (2-2) (100 mg, 0.262 mmol) prepared in Preparation Example 1-1 at −25° C. Formation of slurry was observed, and after slowly raising the temperature to room temperature, the result was stirred for 12 hours at room temperature. TiCl$_4$.DME (1.0 eq.) was added dropwise thereto at −25° C., and the result was stirred for 12 hours at room temperature. The temperature was lowered to −25° C., and MeMgBr (0.18 ml, 3.0 M, 2.05 eq.) was slowly added thereto while stirring. The result was reacted for 12 hours while raising the temperature to room temperature. After completing the reaction, the solvent was removed under vacuum, the result was dissolved in toluene, then filtered, and the filtrate was taken. The toluene was removed under vacuum to obtain a transition metal compound (1-1) in a dark reddish brown solid form (obtained amount=95.9 mg, yield=80%).

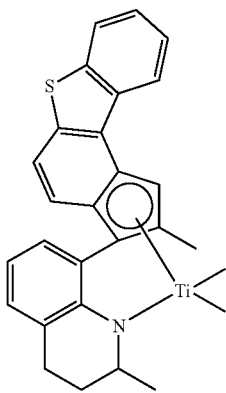

(1-1)

Preparation Example 2-2: Preparation of Transition Metal Compound

In a dry box, n-BuLi (0.54 mmol, 2.05 eq.) was slowly added dropwise to the ligand (2-1) (100 mg, 0.26 mmol) prepared in Preparation Example 1-2 at −25° C. Formation of slurry was observed, and after slowly raising the temperature to room temperature, the result was stirred for 12 hours at room temperature. TiCl$_4$.DME (73.3 mg, 0.26 mmol, 1.0 eq.) was added dropwise thereto at −25° C., and the result was stirred for 12 hours at room temperature. The temperature was lowered to −25° C., and MeMgBr (0.18 ml, 3.0 M, 0.54 mmol) was slowly added thereto while stirring. The result was reacted for 12 hours while raising the temperature to room temperature. After completing the reaction, the solvent was removed under vacuum, the result was dissolved in hexane, then filtered, and the filtrate was taken. The hexane was removed under vacuum to obtain a [8-(1,2-dimethyl-1H-benzo[b]indeno[4,5-d]thiophen-3-yl)-1,2,3,4-tetrahydroquinoline] titanium dimethyl transition metal compound (1-2) in a dark reddish brown solid form (obtained amount=23.3 mg, yield=19%).

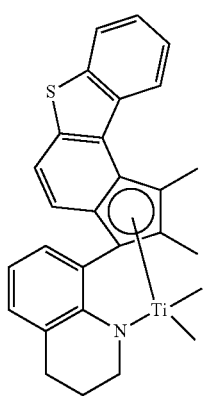

(1-2)

$^1$H NMR (CDCl$_3$): δ −0.61 (s, 3H, Ti—CH$_3$), 0.50 (s, 3H, Ti—CH$_3$), 1.90~1.97 (m, 2H, THQ-CH$_2$), 1.96 (s, 3H, Cp-CH$_3$), 2.75 (t, 2H, THQ-CH$_2$), 3.16 (s, 3H, Cp-0113), 4.44~4.62 (m, 2H, THQ-CH$_2$), 6.85 (t, 1H, aromatic), 7.06 (t, 2H, aromatic), 7.13 (d, 1H, aromatic), 7.40 (d, 1H, aromatic), 7.46 (d, 1H, aromatic), 7.53 (t, 1H, aromatic), 7.94 (d, 111, aromatic), 9.00 (d, 1H, aromatic) ppm Preparation Example 2-3: Preparation of Transition Metal Compound In a dry box, n-BuLi (0.67 mmol, 2.05 eq.) was slowly added dropwise to the ligand (2-3) (130 mg, 0.33 mmol) prepared in Preparation Example 1-3 at −25° C. Formation of slurry was observed, and after slowly raising the temperature to room temperature, the result was stirred for 12 hours at room temperature. TiCl$_4$.DME (92.1 mg, 0.33 mmol, 1.0 eq.) was added dropwise thereto at −25° C., and the result was stirred for 12 hours at room temperature. The temperature was lowered to −25° C., and MeMgBr (0.22 ml, 3.0 M, 0.67 mmol) was slowly added thereto while stirring. The result was reacted for 12 hours while raising the temperature to room temperature. After completing the reaction, the solvent was removed under vacuum, the result was dissolved in toluene, then filtered, and the filtrate was taken. The toluene was removed under vacuum to obtain a [8-(1,2-dimethyl-1H-benzo[b]indeno[4,5-d]thiophen-3-yl)-2-methyl-1,2,3,4-tetrahydroquinoline] titanium dimethyl transition metal compound (1-3) in a dark reddish brown solid form (obtained amount-119.3 mg, yield-77%).

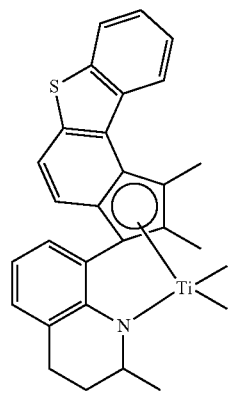

(1-3)

$^1$H NMR (CDCl$_6$): δ −0.57 (s, 3H, Ti—CH$_5$), 0.53 (s, 3H, Ti—CH$_5$), 1.11 (m, 3H, 2-Me-THQ-CH$_5$), 1.88 (s, 3H, Cp-CH$_5$), 1.88~1.90 (m, 2H, 2-Me-THQ), 2.58~2.68 (m, 1H, 2-Me-THQ-CH$_2$), 2.86~2.93 (m, 1H, 2-Me-THQ), 3.23 (s, 3H, Cp-CH$_5$), 5.42 (m, 1H, 2-Me-THQ), 6.85~7.55 (m, 8H, aromatic), 7.95 (d, 2H, aromatic), 9.04 (d, 1H, aromatic) ppm Preparation Example 2-4: Preparation of Transition Metal Compound In a dry box, n-BuLi (0.81 mmol, 2.05 eq.) was slowly added dropwise to the ligand (2-4) (150 mg, 0.39 mmol) prepared in Preparation Example 1-4 at −25° C. Formation of slurry was observed, and after slowly raising the temperature to room temperature, the result was stirred for 12 hours at room temperature. TiCl$_4$.DME (110.0 mg, 0.39 mmol, 1.0 eq.) was added dropwise thereto at −25° C., and the result was stirred for 12 hours at room temperature. The temperature was lowered to −25° C., and MeMgBr (0.27 ml, 3.0 M, 0.81 mmol) was slowly added thereto while stirring. The result was reacted for 12 hours while raising the temperature to room temperature. After completing the reaction, the solvent was removed under vacuum, the result was dissolved in toluene, then filtered, and the filtrate was taken. The toluene was removed under vacuum to obtain a [7-(1,2-dimethyl-1H-benzo[b]indeno[4,5-d]thiophen-3-yl)-2-methylindoline] titanium dimethyl transition metal compound (1-4) in a dark reddish brown solid form (obtained amount-131.8 mg, yield=73%).

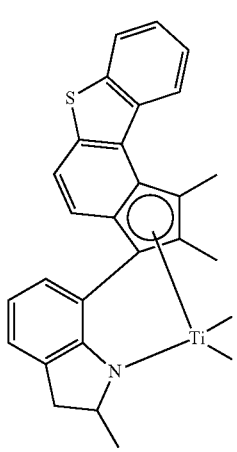

(1-4)

$^1$H NMR (CDCl$_3$): δ −0.46 (s, 3H, Ti—CH$_3$), 0.67 (s, 3H, Ti—CH$_3$), 1.60 (d, 3H, 2-MI-CH$_3$), 2.02 (s, 3H, Cp-CH$_3$), 2.60~2.68 (m, 1H, 2-MI), 3.17~3.24 (m, 1H, 2-MI-CH$_2$), 3.18 (s, 3H, Cp-CH$_3$), 5.05~5.13 (m, 1H, 2-MI), 6.82 (t, 2H, aromatic), 7.09~7.53 (m, 4H, aromatic), 7.94 (d, 2H, aromatic), 8.99 (d, 1H, aromatic) ppm

Example 1: Preparation of Ethylene and 1-Octene Copolymer

To a 2 L autoclave reactor, a hexane (1.0 L) solvent and 210 ml of 1-octene were added, and the temperature of the reactor was raised to 150° C. At the same time, inside the reactor was saturated with approximately 35 bar of ethylene. A catalyst-injection cylinder was filled with the transition metal compound (2 μmol) of Preparation Example 2-1 treated with triisobutyl aluminum (1.0 M), and a dimethyl anilinium tetrakis(pentafluorophenyl)borate co-catalyst (25 equivalents), and the result was injected into the reactor. Herein, the copolymerization reaction was progressed for 8 minutes while constantly injecting ethylene so as to maintain the pressure inside the reactor at approximately 35 bar. After completing the polymerization reaction, the remaining ethylene gas was exhausted, and the polymer solution was added to an excess amount of ethanol to induce precipitation. The obtained polymer was washed 3 times each with ethanol and acetone, and dried for 12 hours or longer in a 80° C. vacuum oven.

Examples 2 to 4: Preparation of Ethylene and 1-Octene Copolymer

Copolymerization was carried out in the same manner as in Example 1 except that each of the transition metal compounds prepared in Preparation Examples 2-2 to 2-4 was used instead of the transition metal compound prepared in Preparation Example 2-1.

Comparative Example: Preparation of Ethylene and 1-Octene Copolymer

Copolymerization was carried out in the same manner as in Example 1 except that a transition metal compound (i) of the following structure was used instead of the transition metal compound prepared in Preparation Example 2-1. Herein, the following transition metal compound was prepared using a method described in Patent No. 0976131.

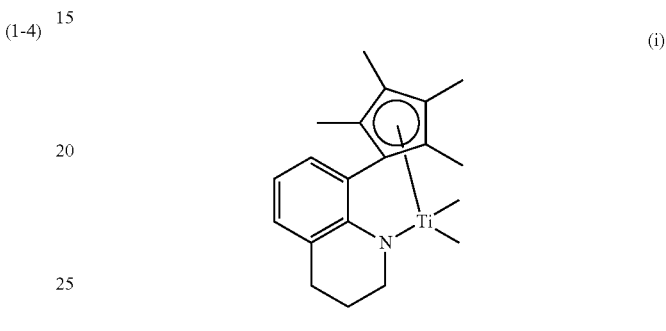

(i)

Test Example 1: Physical Property Evaluation

Catalytic activity in preparing the ethylene and 1-octene copolymers according to Examples 1 to 4 and Comparative Example, and a melt index (MI), density, a crystallization temperature (Tc) and a melting temperature (Tm) of the prepared copolymers were each measured using methods as follows, and the results are shown in the following Table 1.

(1) Catalytic activity: obtained from an introduced molar ratio of the transition metal compound with respect to the total amount of the obtained copolymer prepared. In detail, a ratio of the value obtained from measuring a mass of some of the reaction solution taken after the completion of the polymerization reaction, and the value obtained from measuring a mass of the copolymer remaining after removing all the hexane solvent and residual monomers by heating some of the copolymer for 10 minutes at 120° C. was calculated, and, based thereon, catalytic activity was calculated using the mass of the copolymer produced, the molar number of the transition metal compound used in the polymerization reaction, and the polymerization time.

(2) Melt index (MI): measured in accordance with the ASTM D-1238 (condition E, 190° C., 2.16 Kg load).

(3) Density: the sample treated with an antioxidant (1,000 ppm) was prepared to a sheet having a thickness of 3 mm and a radius of 2 cm using a 180° C. press mold, cooled by 10° C./min, and measured in a Mettler balance.

(4) Crystallization temperature (Tc) and melting temperature (Tm): measured using a differential scanning calorimeter (DSC) 2920 manufactured by TA Corporation. In detail, using DSC, the temperature of the copolymer was raised to 200° C. under nitrogen atmosphere, maintained for 5 minutes, and then lowered to 30° C., and then raised again to observe a DSC curve. Herein, the heating rate and the cooling rate were each 10° C./min. In the measured DSC curve, the crystallization temperature was a maximum point of the exothermic peak in the cooling, and the melting temperature was a maximum point of the endothermic peak in the second temperature raising.

TABLE 1

| | Catalytic Activity (kg/mmol (Ti)) | MI (g/10 min) | Density (g/cc) | Tc (° C.) | Tm (° C.) |
|---|---|---|---|---|---|
| Comparative Example | 29 | 11 | 0.870 | 40 | 60 |
| Example 1 | 11 | 2 | 0.862 | 18 | 34 |
| Example 2 | 15 | 30 | 0.859 | 18 (70) | 34 (114) |
| Example 3 | 25 | 7 | 0.862 | 35 | 36 (112) |
| Example 4 | 12 | 1 | 0.866 | 34 (70) | 51 (117) |

In Table 1, the reason of Tc and Tm each having two values as in Example 2 and 4 is that, in the catalyst compound used in preparing the copolymer of ethylene and 1-octene, the catalyst compound had a chiral center due to the presence of a methyl group locating next to the nitrogen atom causing changes in the catalyst steric property, and as a result, a different type of copolymer of ethylene and 1-octent was produced. In addition, for the same reason as in Examples 2 and 4, two Tm peaks and two Tc peaks also appeared in Example 3, however, in the case of Tc, intensity of one peak was low and its numerical value was not able to be identified. Meanwhile, in Example 1, one Tc peak and one Tm peak were observed due to a difference in the structure in which the dibenzothiophene-fused cyclopentadienyl ring group is substituted with only one methyl group.

As shown in Table 1, the copolymers of 1-octene and ethylene of Examples 1 to 4 prepared using the catalyst composition including the transition metal compound according to the present disclosure exhibited lower density, and lower Tc and Tm compared to the copolymer of Comparative Example. From such results, it can be seen that the transition metal compounds according to the present disclosure very stably maintain the metal site surroundings in a rigid pentagonal ring structure by the amino group linked to the phenylene bridge in a ring form, and thereby structurally facilitate monomer approaches, and accordingly, have relatively excellent reactivity for olefin monomers having large steric hindrance such as 1-octene, and are capable of preparing very low density olefin-based polymers having density of 0.866 g/cc or less together with low Tc and Tm.

What is claimed is:

1. A transition metal compound of the following Chemical Formula 1:

[Chemical Formula 1]

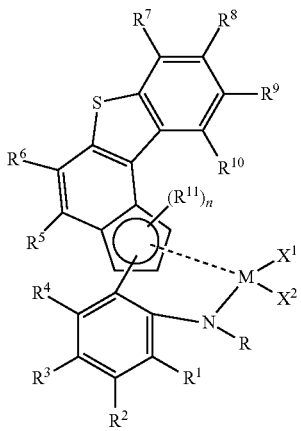

wherein, in Chemical Formula 1,

M is a group 4 transition metal;

R is selected from the group consisting of a hydrogen atom, an alkyl group having 1 to 20 carbon atoms, a cycloalkyl group having 3 to 20 carbon atoms, an aryl group having 6 to 20 carbon atoms, an arylalkyl group having 7 to 20 carbon atoms, and an alkylaryl group having 7 to 20 carbon atoms; or R and $R^1$ are linked to each other to form an aliphatic ring having 3 to 20 carbon atoms or an aromatic ring having 5 to 20 carbon atoms including N;

$R^1$ to $R^{10}$ are each independently selected from the group consisting of a hydrogen atom, a halogen group, an alkyl group having 1 to 20 carbon atoms, an alkenyl group having 2 to 20 carbon atoms, a cycloalkyl group having 3 to 20 carbon atoms, an aryl group having 6 to 20 carbon atoms, an arylalkyl group having 7 to 20 carbon atoms, an alkylaryl group having 7 to 20 carbon atoms, an alkoxy group having 1 to 20 carbon atoms, an aryloxy group having 6 to 20 carbon atoms, a silyl group and combinations thereof, or two or more adjacent functional groups among $R^1$ to $R^{10}$ are linked to each other to form an aliphatic ring having 3 to 20 carbon atoms or an aromatic ring having 6 to 20 carbon atoms;

$R^{11}$ is selected from the group consisting of a hydrogen atom, an alkyl group having 1 to 20 carbon atoms, an alkenyl group having 2 to 20 carbon atoms, a cycloalkyl group having 3 to 20 carbon atoms, an aryl group having 6 to 20 carbon atoms, an arylalkyl group having 7 to 20 carbon atoms, an alkylaryl group having 7 to 20 carbon atoms, a silyl group, and a metalloid radical of a group 14 metal substituted with a hydrocarbyl group having 1 to 20 carbon atoms;

$X^1$ and $X^2$ are each independently selected from the group consisting of a halogen group, an alkyl group having 1 to 20 carbon atoms, an alkenyl group having 2 to 20 carbon atoms, an aryl group having 6 to 20 carbon atoms, an alkylaryl group having 7 to 20 carbon atoms, an arylalkyl group having 7 to 20 carbon atoms, an alkylamino group having 1 to 20 carbon atoms, an arylamino group having 6 to 20 carbon atoms and an alkylidene group having 1 to 20 carbon atoms;

R, $R^1$ to $R^{11}$, $X^1$ and $X^2$ are each independently unsubstituted or substituted with one or more substituents selected from the group consisting of a halogen group, an alkyl group having 1 to 20 carbon atoms, a haloalkyl group having 1 to 20 carbon atoms, an alkenyl group having 2 to 20 carbon atoms, an alkoxy group having 1 to 20 carbon atoms, a cycloalkyl group having 3 to 20 carbon atoms, an aryl group having 6 to 20 carbon atoms, an arylalkyl group having 7 to 20 carbon atoms, an alkylaryl group having 7 to 20 carbon atoms and an aryloxy group having 6 to 20 carbon atoms;

n is an integer of 1 or 2, and when n is an integer of 2, $R^{11}$'s are the same as or different from each other; and wherein a dashed line to the cyclopentadienyl ring represents an η5-complex with the cyclopentadienyl ring, and a solid line to the cyclopentadienyl ring represents a σ-bond to a carbon of the cyclopentadienyl ring.

2. The transition metal compound of claim 1, wherein R is selected from the group consisting of a hydrogen atom, an alkyl group having 1 to 6 carbon atoms, a cycloalkyl group having 3 to 6 carbon atoms, an aryl group having 6 to 12 carbon atoms, an arylalkyl group having 7 to 12 carbon atoms, and an alkylaryl group having 7 to 12 carbon atoms; or R and $R^1$ are linked to each other to for a substituted or unsubstituted aliphatic ring having 4 to 6 carbon atoms or aromatic ring having 4 to 6 carbon atoms including N.

3. The transition metal compound of claim 1, which is selected from the group consisting of compounds of the following Chemical Formulae 1a to 1c:

[Chemical Formula 1a]

[Chemical Formula 1b]

[Chemical Formula 1c]

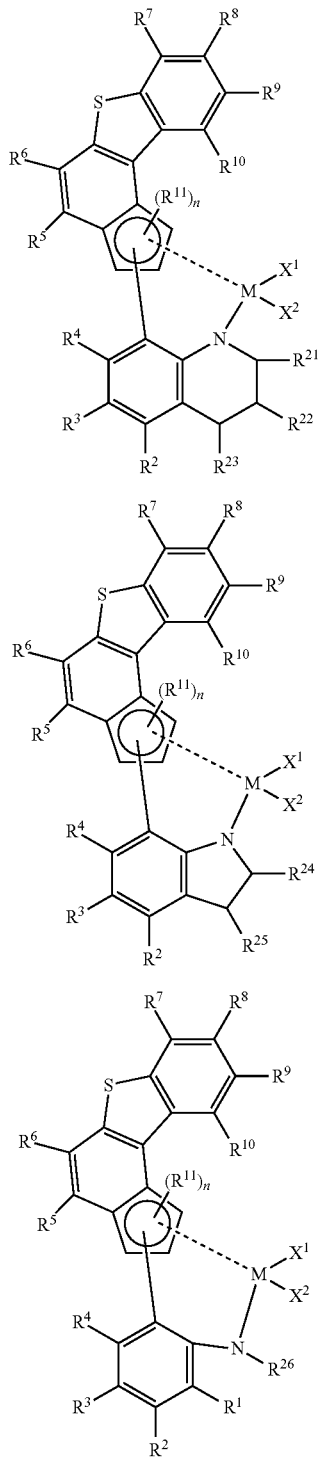

wherein, in Chemical Formulae 1a to 1c,
$R^{21}$ to $R^{25}$ are each independently selected from the group consisting of a hydrogen atom, a halogen group, an alkyl group having 1 to 20 carbon atoms, a haloalkyl group having 1 to 20 carbon atoms, an alkenyl group having 2 to 20 carbon atoms, an alkoxy group having 1 to 20 carbon atoms, a cycloalkyl group having 3 to 20 carbon atoms, an aryl group having 6 to 20 carbon atoms, an arylalkyl group having 7 to 20 carbon atoms, an alkylaryl group having 7 to 20 carbon atoms, and an aryloxy group having 6 to 20 carbon atoms, or two or more adjacent functional groups among $R^{21}$ to $R^{25}$ are linked to each other to form a substituted or unsubstituted aliphatic ring having 3 to 20 carbon atoms or aromatic ring having 5 to 20 carbon atoms;

$R^{26}$ is selected from the group consisting of a hydrogen atom, an alkyl group having 1 to 20 carbon atoms, a cycloalkyl group having 3 to 20 carbon atoms, an aryl group having 6 to 20 carbon atoms, an arylalkyl group having 7 to 20 carbon atoms, and an alkylaryl group having 7 to 20 carbon atoms, and $R^{26}$ is also unsubstituted or substituted with one or more substituents selected from the group consisting of a halogen group, an alkyl group having 1 to 10 carbon atoms, a haloalkyl group having 1 to 10 carbon atoms, an alkenyl group having 2 to 10 carbon atoms, an alkoxy group having 1 to 10 carbon atoms, a cycloalkyl group having 3 to 12 carbon atoms, an aryl group having 6 to 12 carbon atoms, an arylalkyl group having 7 to 12 carbon atoms, an alkylaryl group having 7 to 12 carbon atoms and an aryloxy group having 6 to 12 carbon atoms;

M, $R^1$ to $R^{11}$, $X^1$, $X^2$, and n have the same definitions as in claim 1; and wherein a dashed line to the cyclopentadienyl ring represents an η5-complex with the cyclopentadienyl ring, and a solid line to the cyclopentadienyl ring represents a σ-bond to a carbon of the cyclopentadienyl ring.

4. The transition metal compound of claim 3, wherein M is selected from the group consisting of titanium (Ti), zirconium (Zr) and hafnium;

$R^1$ to $R^{10}$ are each independently selected from the group consisting of a hydrogen atom, an alkyl group having 1 to 6 carbon atoms, an alkenyl group having 2 to 6 carbon atoms, a cycloalkyl group having 3 to 6 carbon atoms, an aryl group having 6 to 12 carbon atoms, an arylalkyl group having 7 to 12 carbon atoms and an alkylaryl group having 7 to 12 carbon atoms, or two or more adjacent functional groups among $R^1$ to $R^{10}$ are linked to each other to form an aliphatic ring having 4 to 6 carbon atoms or an aromatic ring having 6 to 8 carbon atoms;

$R^{11}$ is a hydrogen atom or an alkyl group having 1 to 6 carbon atoms;

$R^{21}$ to $R^{25}$ are each independently selected from the group consisting of a hydrogen atom, an alkyl group having 1 to 6 carbon atoms, an alkenyl group having 2 to 6 carbon atoms, a cycloalkyl group having 3 to 6 carbon atoms, an aryl group having 6 to 12 carbon atoms, an arylalkyl group having 7 to 12 carbon atoms and an alkylaryl group having 7 to 12 carbon atoms, or two or more adjacent functional groups among $R^{21}$ to $R^{25}$ are linked to each other to form an aliphatic ring having 4 to 6 carbon atoms or an aromatic ring having 6 to 8 carbon atoms unsubstituted or substituted with one or more substituents selected from the group consisting of a halogen group, an alkyl group having 1 to 10 carbon atoms and a haloalkyl group having 1 to 10 carbon atoms;

$R^{26}$ is selected from the group consisting of a hydrogen atom, an alkyl group having 1 to 6 carbon atoms, a cycloalkyl group having 3 to 12 carbon atoms, an aryl group having 6 to 12 carbon atoms, an arylalkyl group having 7 to 12 carbon atoms, and an alkylaryl group having 7 to 12 carbon atoms, and unsubstituted or substituted with one or more substituents selected from the group consisting of a halogen group, an alkyl group having 1 to 10 carbon atoms and a haloalkyl group having 1 to 10 carbon atoms;

$X^1$ and $X^2$ are each independently an alkyl group having 1 to 6 carbon atoms; and n is an integer of 1 or 2, and when n is an integer of 2, $R^{11}$s are the same as or different from each other.

5. The transition metal compound of claim 1, which is selected from the group consisting of compounds of the following Chemical Formulae 1-1 to 1-12:

(1-1)

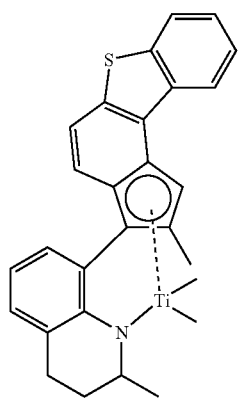

(1-2)

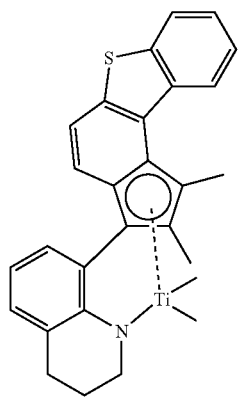

(1-3)

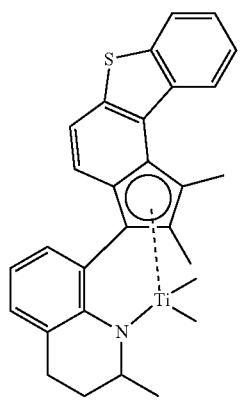

(1-4)

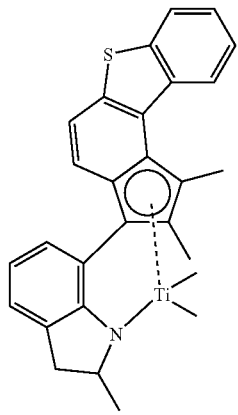

(1-5)

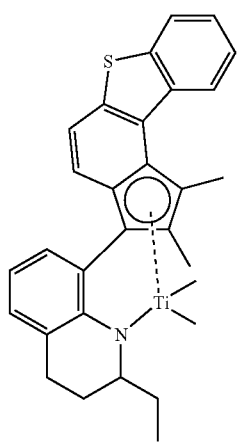

(1-6)

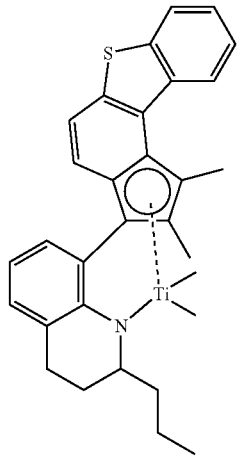

(1-7)
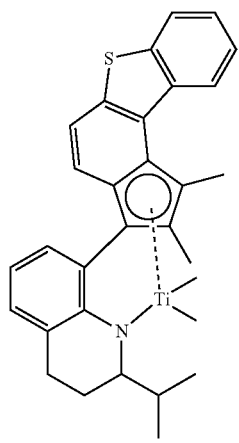
(1-8)
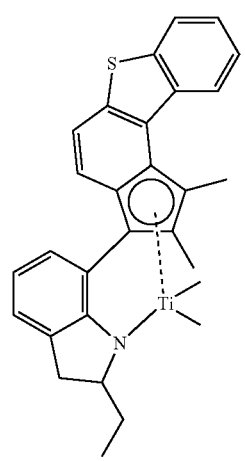
(1-9)
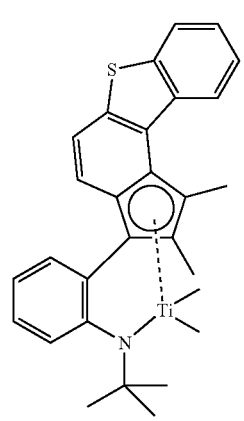
(1-10)
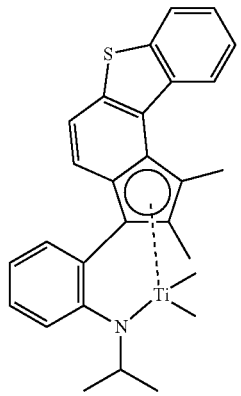
(1-11)
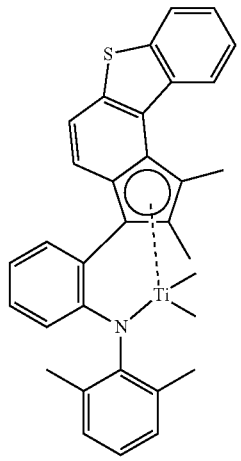
(1-12)
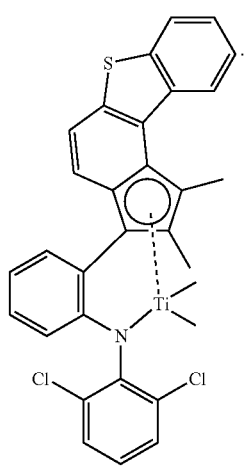
6. A catalyst composition comprising the transition metal compound of claim 1.
7. The catalyst composition of claim 6, further comprising at least one co-catalyst selected from the group consisting of compounds of the following Chemical Formulae 8 to 11:
$$-[Al(R^{31})-O]_a-\quad\quad\text{[Chemical Formula 8]}$$
$$A(R^{32})_3\quad\quad\text{[Chemical Formula 9]}$$

$[L-H]^+[W(D)_4]^-$ [Chemical Formula 10]

$[L]^+[W(D)_4]^-$ [Chemical Formula 11]

wherein, in Chemical Formulae 8 to 11, $R^{31}$ and $R^{32}$ are each independently selected from the group consisting of a halogen group, a hydrocarbyl group having 1 to 20 carbon atoms, and a hydrocarbyl group having 1 to 20 carbon atoms substituted with a halogen group;

A is aluminum or boron;

Ds are each independently an aryl group having 6 to 20 carbon atoms or an alkyl group having 1 to 20 carbon atoms in which one or more hydrogen atoms may be substituted with a substituent, and herein, the substituent is at least any one selected from the group consisting of a halogen group, a hydrocarbyl group having 1 to 20 carbon atoms, an alkoxy group having 1 to 20 carbon atoms and an aryloxy group having 6 to 20 carbon atoms;

H is a hydrogen atom;

L is a neutral or cationic Lewis acid;

W is a group 13 element; and a is an integer of 2 or greater.

\* \* \* \* \*